US009051578B2

(12) United States Patent
Puthigae et al.

(10) Patent No.: US 9,051,578 B2
(45) Date of Patent: Jun. 9, 2015

(54) METHODS AND COMPOSITIONS FOR PLANT IMPROVEMENT

(75) Inventors: Sathish Puthigae, Auckland (NZ); Margaret Biswas, Auckland (NZ); Catherine Jane Bryant, Auckland (NZ); Shivendra Bajaj, Auckland (NZ); Kerry Robert Templeton, Auckland (NZ)

(73) Assignee: Insight Genomics Limited, Hamilton (NZ)

( * ) Notice: Subject to any disclaimer, the term of this patent is extended or adjusted under 35 U.S.C. 154(b) by 1059 days.

(21) Appl. No.: 12/994,739

(22) PCT Filed: May 26, 2009

(86) PCT No.: PCT/NZ2009/000090
§ 371 (c)(1),
(2), (4) Date: Apr. 25, 2011

(87) PCT Pub. No.: WO2009/145645
PCT Pub. Date: Dec. 3, 2009

(65) Prior Publication Data
US 2011/0209250 A1 Aug. 25, 2011

Related U.S. Application Data

(60) Provisional application No. 61/056,583, filed on May 28, 2008.

(51) Int. Cl.
*C07K 14/415* (2006.01)
*C12N 15/29* (2006.01)
*C12N 15/82* (2006.01)
*C12N 15/63* (2006.01)

(52) U.S. Cl.
CPC ............ *C12N 15/8273* (2013.01); *C12N 15/63* (2013.01); *C12N 15/82* (2013.01); *C07K 14/415* (2013.01); *C12N 15/8271* (2013.01)

(58) Field of Classification Search
None
See application file for complete search history.

(56) References Cited

U.S. PATENT DOCUMENTS

| 4,795,855 | A | 1/1989 | Fillatti et al. |
| 5,004,863 | A | 4/1991 | Umbeck |
| 5,159,135 | A | 10/1992 | Umbeck |
| 5,177,010 | A | 1/1993 | Goldman et al. |
| 5,187,073 | A | 2/1993 | Goldman et al. |
| 5,188,958 | A | 2/1993 | Moloney et al. |
| 5,352,605 | A | 10/1994 | Fraley et al. |
| 5,364,780 | A | 11/1994 | Hershey et al. |
| 5,416,011 | A | 5/1995 | Hinchee et al. |
| 5,463,174 | A | 10/1995 | Moloney et al. |
| 5,510,474 | A | 4/1996 | Quail et al. |
| 5,563,055 | A | 10/1996 | Townsend et al. |
| 5,569,834 | A | 10/1996 | Hinchee et al. |
| 5,591,616 | A | 1/1997 | Hiei et al. |
| 5,750,871 | A | 5/1998 | Moloney et al. |
| 5,792,935 | A | 8/1998 | Arntzen et al. |
| 5,824,877 | A | 10/1998 | Hinchee et al. |
| 5,846,797 | A | 12/1998 | Strickland |
| 5,952,543 | A | 9/1999 | Firoozabady et al. |
| 5,968,830 | A | 10/1999 | Dan et al. |
| 5,981,840 | A | 11/1999 | Zhao et al. |
| 6,020,539 | A | 2/2000 | Goldman et al. |
| 6,037,522 | A | 3/2000 | Dong et al. |
| 6,074,877 | A | 6/2000 | D'Halluin et al. |
| 7,569,389 | B2 * | 8/2009 | Feldmann et al. ............ 435/468 |
| 2004/0034888 | A1 | 2/2004 | Liu et al. |
| 2004/0123343 | A1 | 6/2004 | La Rosa et al. |
| 2004/0172684 | A1 | 9/2004 | Kovalic et al. |
| 2004/0214272 | A1 | 10/2004 | La Rosa et al. |
| 2006/0123505 | A1 | 6/2006 | Kikuchi et al. |
| 2007/0020621 | A1 | 1/2007 | Boukharov et al. |
| 2007/0044171 | A1 * | 2/2007 | Kovalic et al. ................ 800/278 |
| 2007/0067865 | A1 | 3/2007 | Kovalic et al. |
| 2007/0124833 | A1 | 5/2007 | Abad et al. |
| 2010/0242134 | A1 | 9/2010 | Puthigae et al. |
| 2010/0293664 | A1 | 11/2010 | Puthigae et al. |
| 2011/0179517 | A1 | 7/2011 | Puthigae et al. |
| 2011/0185452 | A1 | 7/2011 | Puthigae et al. |

FOREIGN PATENT DOCUMENTS

| WO | 01/04285 | 1/2001 |
| WO | 02/00894 | 3/2002 |

(Continued)

OTHER PUBLICATIONS

Jain et al. Overexpression of putative topoisomerase 6 genes from rice confers stress tolerance in transgenic *Arabidopsis* plants. FEBS Journal. 2006. 273. 5245-5260.*
Anderson, O. (Aug. 21, 2000) Genbank Accession No. BE604232.1, "WHE1413-1416_M14_M14ZS Wheat drought stressed leaf cDNA library *Triticum aestivum* cDNA clone WHE1413-1416_M14_M14, mRNA sequence".
Anderson, O. (Aug. 21, 2000) Genbank Accession No. BE604673.1, "WHE1413-1416_J06_J06ZS Wheat drought stressed leaf cDNA library *Triticum aestivum* cDNA clone WHE1413-1416_J06_J06, mRNA sequence.".
Bohlmann, J. (Jun. 22, 2004) Genbank Accession No. CO227877.1, "WS-ES-A-1 *Picea glauca* cDNA clone WS0013_B01 3-, mRNA sequence".

(Continued)

*Primary Examiner* — Anne Kubelik
*Assistant Examiner* — Ashley K Buran
(74) *Attorney, Agent, or Firm* — Lathrop & Gage LLP

(57) ABSTRACT

The invention provides an isolated polynucleotide comprising the sequence of SEQ ID NO: 1 or a variant thereof, wherein the variant encodes a polypeptide capable of modulating in a plant tolerance to at least one environmental stress selected from drought, cold, freezing, heat and salinity. The invention also provides construct, vectors, host cells, plant cells and plants genetically modified to comprise the polynucleotide. The invention also provides methods for producing and selecting plants that are tolerant to at least one environmental stress selected from drought, cold, freezing, heat and salinity, making use of the polynucleotides of the invention.

7 Claims, 15 Drawing Sheets

(56) References Cited

FOREIGN PATENT DOCUMENTS

| WO | 02/50294 | 6/2002 |
|---|---|---|
| WO | 03/031631 | 4/2003 |
| WO | 2004/058963 | 7/2004 |
| WO | 2005/049835 | 6/2005 |
| WO | 2005/123919 | 12/2005 |
| WO | 2007/049275 | 5/2007 |
| WO | 2007/078286 | 7/2007 |

OTHER PUBLICATIONS

Cordonnier-Pratt, M.M. (Oct. 17, 2003) Genbank Accession No. CF760284.1, "DSAF1_57_ $_{G11.b1}$_A011 Drought-stressed after flowering *Sorghum* bicolor cDNA clone DSAF1_57_G11_A011 5-, mRNA sequence".

Nahm, B.H. (May 31, 2007) Genbank Accession No. CV726210.1, "14Salt—03-L17.b1 Salt treated rice leaf *Lambda phage* cDNA library (14Salt) *Oryza sativa* Japonica Group cDNA clone 14Salt—03-L17, mRNA sequence".

Palenik et al. (Apr. 19, 2007) Genbank Accession No. XM_001420059, "*Ostreococcus lucimarinus* CCE9901 predicted protein (OSTLU_37980) mRNA, complete cds".

Shin-I, T.(Jun. 14, 2005) Genbank Accession No. BJ956253.1, "pphf full-length cDNA library *Physcomitrella patens* subsp. patens cDNA clone pphf2a01 3-, mRNA sequence".

Tuskan et al. (Sep. 12, 2006) Genbank Accession No. XM_002311979.1, "*Populus trichocarpa* predicted protein, mRNA".

Waugh et al. (Jul. 23, 2002) Genbank Accession No. BM371137.2, "EBro04_SQ003_J15_R root, 3 week, salt-stressed, cv Optic, EBro04 *Hordeum vulgare* subsp. vulgare cDNA clone EBro04_SQ003_J15 5-, mRNA sequence".

Wing, R.A. (Oct. 22, 2001) Genbank Accession No. BF629983.2, "HVSMEb0007124f *Hordeum vulgare* seedling shoot EST library HVcDNA0002 (Dehydration stress) *Hordeum vulgare* subsp. vulgare cDNA clone HVSMEb0007124f, mRNA sequence".

Wing, R.A. (Oct. 22, 2001) Genbank Accession No. BF629247.2, "HVSMEb0010H20f *Hordeum vulgare* seedling shoot EST library HVcDNA0002 (Dehydration stress) *Hordeum vulgare* subsp. vulgare cDNA clone HVSMEb0010H20f, mRNA sequence".

Yazaki, S. (Mar. 14, 2005) Genbank Accession No. AU248661.1, "*Lolium multiflorum* cDNA clone HL012D12-5, mRNA sequence".

Yu et al. (Jul. 24, 2007) EMBL Accession No. A6N069_ORYSI, "The genomes of *Oryza sativa*: a history of duplications."

Birch, R.G. (1997) "Plant Transformation: Problems and Strategies for Practical Application," Ann Rev Plant Phys Plant Mol Biol, 48:297-326.

Bowie et al. (1990) "Deciphering the Message in Protein Sequences: Tolerance to Amino Acid Substitutions," Science 247:1306-1310.

Falquet et al. (2002) "The PROSITE database, its status in 2002," Nucleic Acids Res. 30(1):235-238.

Frohman, M.A. (1993) "Rapid Amplification of complementary DNA Ends for Generation of full-length Complementary DNAs: Thermal RACE," Methods Enzymol. 218:340-356.

Gruber et al. (1993) "Vectors for Plant Transformation," Methods in Plant Mol. Biol. and Biotech, pp. 89-119, CRC Press.

Hofmann et al. (1999) "The PROSITE database, its status in 1999," Nucleic Acids Res. 27(1):215-219.

Horsch et al. (1985) "A Simple and General Method for transferring Genes into Plants," Science 227:1229-1231.

Huang, X. (1994) "On Global Sequence Alignment," Comp. Apps in the Biosciences 10(3):227-235.

Jones et al. (1998) "The effect of chimeric transgene architecture on co-ordinated gene silencing," Planta 204:499-505.

Kumar et al., 1996 "Potato plants expressing antisense and sense S-adenosylmethionine decarboxylase (SAMDC) transgenes show altered levels of polyamines and ethylene: antisense plants display abnormal phenotypes," Plant J. 9(2):147-158.

Llave et al. (2002) "Cleavage of Scarecrow-like mRNA Targets Directed by a Class of *Arabidopsis* miRNA," Science 297:2053-2056.

McIntyre et al. (1996) "Strategies for the suppression of peroxidase gene expression in tobacco. I. Designing efficient ribozymes," Transgenic Res. 5:257-262.

Nielsen et al. (1991) "Sequence-Selective Recognition of DNA by Strand Displacement with a Thymine-Substituted Polyamide," Science 254:1497-1500.

Schrott, M. (1995) "Selectable Marker and Reporter Genes," Gene Transfer to Plants, Potrykus T., Spangenbert. Eds., Springer Verlag. Berline, pp. 325-336.

Triglia et al. (1988) "A procedure for in vitro amplification of DNA segments that lie outside the boundaries of known sequences," Nucleic Acids Res. 16(16):8186.

Tuskan et al. (2006) "The genome of black cottonwood, *Populus trichocarpa* (Torr. & Gray)," Science 313(5793):1596-1604.

\* cited by examiner

```
ggaattcgatatcaagcttggcactggccgtcgttttacaacgtcgtgactgggaaaaccctggcg
ttacccaacttaatcgccttgcagcacatccccctttcgccagctggcgtaatagcgaagaggccc
gcaccgatcgcccttcccaacagttgcgcagcctgaatggcgaatgctagagcagcttgagcttgg
atcagattgtcgtttccgccttcagtttaaactatcagtgtttgacaggatatattggcgggtaa
acctaagagaaagagcgtttattagaataacggatatttaaaagggcgtgaaaaggtttatccgt
tcgtccatttgtatgtgcatgccaaccacagggttccctcgggatcaaagtactttgatccaacc
cctccgctgctatagtgcagtcggcttctgacgttcagtgcagccgtcttctgaaaacgacatgtc
gcacaagtcctaagttacgcgacaggctgccgcctgcccttttcctggcgttttcttgtcgcgtg
ttttagtcgcataaagtagaatacttgcgactagaaccggagacattacgccatgaacaagagcgc
cgccgctggcctgctggctatgccgcgtcagcaccgacgaccaggacttgaccaaccaacgggc
cgaactgcacgcggccggctgcaccaagctgttttcgagaagatcaccggcaccaggcgcgaccg
cccggagctggccaggatgcttgaccacctacgccctggcgacgttgtgacagtgaccaggctaga
ccgcctggcccgcagcacccgcgacctactggacattgccgagcgcatccaggaggccggcgcggg
cctgcgtagcctggcagagccgtgggccgacaccaccacgccggccggccgcatggtgttgaccgt
gttcgccggcattgccgagttcgagcgttccctaatcatcgaccgcaccccggagcgggcgcgaggc
cgccaaggcccgaggcgtgaagtttggccccccgccctaccctcaccccggcacagatcgccgacgc
ccgcgagctgatcgaccaggaaggccgcaccgtgaaagaggcggctgcactgcttggcgtgcatcg
ctcgaccctgtaccgcgcacttgagcgcagcgaggaagtgacgcccaccgaggccaggcggcgcgg
tgccttccgtgaggacgcattgaccgaggccgacgccctggcggccgccgagaatgaacgccaaga
ggaacaagcatgaaaccgcaccaggacggccaggacgaaccgttttttcattaccgaagagatcgag
gcggagatgatcgcggccgggtacgtgttcgagccgcccgcgcacgtctcaaccgtgcggctgcat
gaaatcctggccggtttgtctgatgccaagctggcggcctggccggccagcttggccgctgaagaa
accgagcgccgccgtctaaaaaggtgatgtgtatttgagtaaaacagcttgcgtcatgcggtcgct
gcgtatatgatgcgatgagtaaataaacaaatacgcaaggggaacgcatgaaggttatcgctgtac
ttaaccagaaaggcgggtcaggcaagacgaccatcgcaacccatctagcccgcgccctgcaactcg
ccggggccgatgttctgttagtcgattccgatcccagggcagtgcccgcgattgggcggccgtgc
gggaagatcaaccgctaaccgttgtcggcatcgaccgcccgacgattgaccgcgacgtgaaggcca
tcggccggcgacttcgtagtgatcgacggagcgcccaggcggcggacttggctgtgtccgcga
tcaaggcagccgacttcgtgctgattccggtgcagccaagcccttacgacatatgggccaccgccg
acctggtggagctggttaagcagcgcattgaggtcacggatggaaggctacaagcggcctttgtcg
tgtcgcgggcgatcaaaggcacgcgcatcggcggtgaggttgccgaggcgctggccgggtacgagc
tgcccattcttgagtcccgtatcacgcagcgcgtgagctacccaggcactgccgccgccggcacaa
ccgttcttgaatcagaacccgagggcgacgctgcccgcgaggtccaggcgctggccgctgaaatta
aatcaaaactcatttgagttaatgaggtaaagagaaaatgagcaaaagcacaaacacgctaagtgc
cggccgtccgagcgcacgcagcagcaaggctgcaacgttggccagcctggcagacacgccagccat
gaagcgggtcaactttcagttgccggcggaggatcacaccaagctgaagatgtacgcggtacgcca
aggcaagaccattaccgagctgctatctgaatacatcgcgcagctaccagagtaaatgagcaaatg
aataaatgagtagatgaattttagcggctaaaggaggcggcatggaaaatcaagaacaaccaggca
ccgacgccgtggaatgcccatgtgtggaggaacgggcggttggccaggcgtaagcggctggttg
tctgccggccctgcaatggcactggaaccccaagcccgaggaatcggcgtgacggtcgcaaacca
tccggcccggtacaaatcggcgcggcgctgggtgatgacctggtggagaagttgaaggccgcgcag
gccgcccagcggcaacgcatcgaggcagaagcacgccccggtgaatcgtggcaagcggccgctgat
cgaatccgcaaagaatcccggcaaccgccggcagccggtgcgccgtcgattaggaagccgcccaag
ggcgacgagcaaccagatttttttcgttccgatgctctatgacgtgggcacccgcgatagtcgcagc
atcatgacgtggccgttttccgtctgtcgaagcgtgaccgacgagctggcgaggtgatccgctac
gagcttccagacgggcacgtagaggtttccgcagggccggccggcatggccagtgtgtgggattac
gacctggtactgatggcggtttcccatctaaccgaatccatgaaccgataccgggaagggaaggga
gacaagcccggccgcgtgttccgtccacacgttgcggacgtactcaagttctgccggcgagccgat
ggcggaaagcagaaagacgacctggtagaaacctgcattcggttaaacaccacgcacgttgccatg
cagcgtacgaagaaggccaagaacggccgcctggtgacggtatccgagggtgaagccttgattagc
```

FIGURE 2

```
cgctacaagatcgtaaagagcgaaaccgggcggccggagtacatcgagatcgagctagctgattgg
atgtaccgcgagatcacagaaggcaagaacccggacgtgctgacggttcaccccgattactttttg
atcgatcccggcatcggccgttttctctaccgcctggcacgccgcgccgcaggcaaggcagaagcc
agatggttgttcaagacgatctacgaacgcagtggcagcgccggagagttcaagaagttctgtttc
accgtgcgcaagctgatcgggtcaaatgacctgccggagtacgatttgaaggaggaggcggggcag
gctggcccgatcctagtcatgcgctaccgcaacctgatcgagggcgaagcatccgccggttcctaa
tgtacggagcagatgctagggcaaattgccctagcaggggaaaaaggtcgaaaaggtctctttcct
gtggatagcacgtacattgggaacccaaagccgtacattgggaaccggaacccgtacattgggaac
ccaaagccgtacattgggaaccggtcacacatgtaagtgactgatataaaagagaaaaaaggcgat
ttttccgcctaaaactcttttaaaacttattaaaactcttaaaacccgcctggcctgtgcataactg
tctggccagcgcacagccgaagagctgcaaaaagcgcctaccttcggtcgctgcgctccctacgc
cccgccgcttcgcgtcggcctatcgcggccgctggccgctcaaaaatggctggcctacggccaggc
aatctaccagggcgcggacaagccgcgccgtcgccactcgaccgccggcgcccacatcaaggcacc
ctgcctcgcgcgtttcggtgatgacggtgaaaacctctgacacatgcagctcccggagacggtcac
agcttgtctgtaagcggatgccgggagcagacaagcccgtcagggcgcgtcagcgggtgttggcgg
gtgtcggggcgcagccatgacccagtcacgtagcgatagcggagtgtatactggcttaactatgcg
gcatcagagcagattgtactgagagtgcaccatatgcggtgtgaaataccgcacagatgcgtaagg
agaaaataccgcatcaggcgctcttccgcttcctcgctcactgactcgctgcgctcggtcgttcgg
ctgcggcgagcggtatcagctcactcaaaggcggtaatacggttatccacagaatcaggggataac
gcaggaaagaacatgtgagcaaaaggccagcaaaaggccaggaaccgtaaaaaggccgcgttgctg
gcgttttccataggctccgcccccctgacgagcatcacaaaaatcgacgctcaagtcagaggtgg
cgaaacccgacaggactataaagataccaggcgtttccccctggaagctccctcgtgcgctctcct
gttccgaccctgccgcttaccggatacctgtccgcctttctcccttcgggaagcgtggcgctttct
catagctcacgctgtaggtatctcagttcggtgtaggtcgttcgctccaagctgggctgtgtgcac
gaaccccccgttcagcccgaccgctgcgccttatccggtaactatcgtcttgagtccaacccgta
agacacgacttatcgccactggcagcagccactggtaacaggattagcagagcgaggtatgtaggc
ggtgctacagagttcttgaagtggtggcctaactacggctacactagaaggacagtatttggtatc
tgcgctctgctgaagccagttaccttcggaaaaagagttggtagctcttgatccggcaaacaaacc
accgctggtagcggtggtttttttgtttgcaagcagcagattacgcgcagaaaaaaaggatctcaa
gaagatcctttgatcttttctacggggtctgacgctcagtggaacgaaaactcacgttaagggatt
ttggtcatgcattctaggtactaaaacaattcatccagtaaaatataatatttttattttctcccaa
tcaggcttgatccccagtaagtcaaaaaatagctcgacatactgttcttccccgatatcctccctg
atcgaccggacgcagaaggcaatgtcataccacttgtccgccctgccgcttctcccaagatcaata
aagccacttactttgccatctttcacaaagatgttgctgtctcccaggtcgccgtgggaaaagaca
agttcctcttcgggcttttccgtctttaaaaaatcatacagctcgcgcggatctttaaatggagtg
tcttcttcccagttttcgcaatccacatcggccagatcgttattcagtaagtaatccaattcggct
aagcggctgtctaagctattcgtatagggacaatcgatatgtcgatggagtgaaagagcctgatg
cactccgcatacagctcgataatcttttcagggctttgttcatcttcatactcttccgagcaaagg
acgccatcggcctcactcatgagcagattgctccagccatcatgccgttcaaagtgcaggacctt
ggaacaggcagctttccttccagccatagcatcatgtccttttcccgttccacatcataggtggtc
cctttataccggctgtccgtcattttaaatataggttttcattttctcccaccagcttatatacc
ttagcaggagacattccttccgtatcttttacgcagcggtattttcgatcagtttttttcaattcc
ggtgatattctcatttttagccatttattatttccttcctcttttctacagtatttaaagataccc
aagaagctaattataacaagacgaactccaattcactgttccttgcattctaaaaccttaaatacc
agaaaacagcttttcaaagttgttttcaaagttggcgtataacatagtatcgacggagccgattt
tgaaaccgcggtgatcacaggcagcaacgctctgtcatcgttacaatcaacatgctaccctccgcg
agatcatccgtgtttcaaacccggcagcttagttgccgttcttccgaatagcatcggtaacatgag
caaagtctgccgccttacaacggctctcccgctgacgccgtcccggactgatgggctgcctgtatc
gagtggtgattttgtgccgagctgccggtcggggagctgttggctggctggtggcaggatatattg
tggtgtaaacaaattgacgcttagacaacttaataacacattgcggacgtttttaatgtactgaat
taacgccgaattaattcggggggatctggattttagtactggattttggttttaggaattagaaatt
ttattgatagaagtattttacaaatacaaatacactaagggtttcttatatgctcaacacatga
```

FIGURE 2 cont.

```
gcgaaaccctataggaaccctaattcccttatctgggaactactcacacattattatggagaaact
cgagcttgtcgatcgacagatccggtcggcatctactctatttctttgccctcggacgagtgctgg
ggcgtcggtttccactatcggcgagtacttctacacagccatcggtccagacggccgcgcttctgc
gggcgatttgtgtacgcccgacagtcccggctccggatcggacgattgcgtcgcatcgaccctgcg
cccaagctgcatcatcgaaattgccgtcaaccaagctctgatagagttggtcaagaccaatgcgga
gcatatacgccggagtcgtggcgatcctgcaagctccggatgcctccgctcgaagtagcgcgtct
gctgctccatacaagccaaccacggcctccagaagaagatgttggcgacctcgtattgggaatccc
cgaacatcgcctcgctccagtcaatgaccgctgttatgcggccattgtccgtcaggacattgttgg
agccgaaatccgcgtgcacgaggtgccggacttcggggcagtcctcggcccaaagcatcagctcat
cgagagcctgcgcgacggacgacctgacggtgtcgtccatcacagtttgccagtgatacacatggg
gatcagcaatcgcgcatatgaaatcacgccatgtagtgtattgaccgattccttgcggtccgaatg
ggccgaacccgctcgtctggctaagatcggccgcagcgatcgcatccatagcctccgcgaccggtt
gtagaacagcgggcagttcggtttcaggcaggtcttgcaacgtgacaccctgtgcacggcgggaga
tgcaataggtcaggctctcgctaaactcccaatgtcaagcacttccggaatcgggagcgcggccg
atgcaaagtgccgataaacataacgatctttgtagaaaccatcggcgcagctatttacccgcagga
catatccacgccctcctacatcgaagctgaaagcacgagattcttcgccctccgagagctgcatca
ggtcggagacgctgtcgaacttttcgatcagaaacttctcgacagacgtcgcggtgagttcaggct
ttttcatatctcattgcccccccggatctgcgaaagctcgagagagatagatttgtagagagagac
tggtgatttcagcgtgtcctctccaaatgaaatgaacttccttatatagaggaaggtcttgcgaag
gatagtgggattgtgcgtcatcccttacgtcagtggagatatcacatcaatccacttgctttgaag
acgtggttggaacgtcttcttttccacgatgctcctcgtgggtgggggtccatctttgggaccac
tgtcggcagaggcatcttgaacgatagcctttcctttatcgcaatgatggcatttgtaggtgccac
cttccttttctactgtccttttgatgaagtgacagatagctgggcaatggaatccgaggaggtttc
ccgatattaccctttgttgaaaagtctcaatagccctttggtcttctgagactgtatctttgatat
tcttggagtagacgagagtgtcgtgctccaccatgttatcacatcaatccacttgctttgaagacg
tggttggaacgtcttcttttccacgatgctcctcgtgggtgggggtccatctttgggaccactgt
cggcagaggcatcttgaacgatagcctttcctttatcgcaatgatggcatttgtaggtgccaccct
cctttttctactgtccttttgatgaagtgacagatagctgggcaatggaatccgaggaggtttcccg
atattaccctttgttgaaaagtctcaatagccctttggtcttctgagactgtatctttgatattct
tggagtagacgagagtgtcgtgctccaccatgttggcaagctgctctagccaatacgcaaaccgcc
tctccccgcgcgttggccgattcattaatgcagctggcacgacaggtttcccgactggaaagcggg
cagtgagcgcaacgcaattaatgtgagttagctcactcattaggcaccccaggctttacactttat
gcttccggctcgtatgttgtgtggaattgtgagcggataacaatttcacacaggaaacagctatga
ccatgattacgaattcccttaattaataag**agcagcttgccaacatggtggagcacgacactctcg
tctactccaagaatatcaaagatacagtctcagaagaccaaagggctattgagacttttcaacaaa
gggtaatatcgggaaacctcctcggattccattgcccagctatctgtcacttcatcaaaaggacag
tagaaaaggaaggtggcacctacaaatgccatcattgcgataaaggaaaggctatcgttcaagatg
cctctgccgacagtggtcccaaagatggacccccacccacgaggagcatcgtggaaaagaagacg
ttccaaccacgtcttcaaagcaagtggattgatgtgaacatggtggagcacgacactctcgtctac
tccaagaatatcaaagatacagtctcagaaggccaaagggctattgagacttttcaacaaagggta
atatcgggaaacctcctcggattccattgcccagctatctgtcacttcatcaaaaggacagtagaa
aaggaaggtggcacctacaaatgccatcattgcgataaaggaaaggctatcgttcaagatgctctg
ccgacagtggtcccaaagatggacccccacccacgaggagcatcgtggaaaagaagacgttccaa
ccacgtcttcaaagcaagtggattgatgtgatatctccactgacgtaagggatgacgcacaatccc
actatccttcgcaagacccttcctctatataaggaagttcatttcatttggagaggacacgctgaa
atcaccagtctctctctacaaatctatctctctc**cattaggaagagctagggtttggtcgagagga
ggccggcggccgggcgatcgaccgaagatgatcgaggtggtgctcaacgaccgtctggggaagaag
gtgcgcgtcaagtgcaacgaggacgacaccatcggcgacctcaagaagctcgtcgcggcgcagacc
gggaccaggcccgagaagatccgcatccagaagtggtacaccatctacaaggaccacatcaccctc
ggcgactacgagatccacgacggaatgggactcgagctctactacaactagcccattcaatctccc
cagccatgttggtatgcatcccctagccatccctagatgatgtctttggttgtgttccagtccca
gtgtggtcagagttcatgtgtgagctaaaaaaagctactagtattatgtaagtactgcatgaccca
```

FIGURE 2 cont.

tcatgactgttgacagcttgaactttgtgtcctattgtcacccggcctggtttctccataataatg
tgtgagtagttcccagataagggaattagggttcctatagggtttcgctcatgtgttgagcatata
agaaacccttagtatgtatttgtatttgtaaaatacttctatcaataaaatttctaattcctaaaa
ccaaaatccagtactaaaatccagatcccccgaattaattcggcgttaattcagtatcggcgcgcc
ttaattaaggcgcgccctgca (SEQ ID NO:23)

GAAGAGCTAGGGTTTGGTCGAGAGGAGGCCGGCGGCCGGGCGATCGACCGAAGATGATCGAGGTGG
TGCTCAACGACCGTCTGGGGAAGAAGGTGCGCGTCAAGTGCAACGAGGACGACACCATCGGCGACC
TCAAGAAGCTCGTCGCGGCGCAGACCGGGACCAGGCCCGAGAAGATCCGCATCCAGAAGTGGTACA
CCATCTACAAGGACCACATCACCCTCGGCGACTACGAGATCCACGACGGAATGGGACTCGAGCTCT
ACTACAACTAGCCCATTCAATCTCCCCAGCCATGTTGGTATGCATCCCCCTAGCCATCCCTAGA**TG
A**TGTCTTTGGTTGTGTTCCAGTCCCAGTGTGGTCAGAGTTCATGTGTGAGCTAAAAAAAGCTACTA
GTATTATGTAAGTACTGCATGACCCATCATG<u>ACTGTTGACAG</u>CTTGAACTTTGTGTCCTATTGTCA
CCC (SEQ ID NO:1)

Figure 11

```
                        SEQUENCE LISTING

<160> NUMBER OF SEQ ID NOS: 34

<210> SEQ ID NO 1
<211> LENGTH: 465
<212> TYPE: DNA
<213> ORGANISM: Lolium perenne

<400> SEQUENCE: 1
gaagagctag ggtttggtcg agaggaggcc ggcggccggg cgatcgaccg aagatgatcg      60
aggtggtgct caacgaccgt ctggggaaga aggtgcgcgt caagtgcaac gaggacgaca     120
ccatcggcga cctcaagaag ctcgtcgcgg cgcagaccgg gaccaggccc gagaagatcc     180
gcatccagaa gtggtacacc atctacaagg accacatcac cctcggcgac tacgagatcc     240
acgacggaat gggactcgag ctctactaca actagcccat tcaatctccc cagccatgtt     300
ggtatgcatc ccctagcca tccctagatg atgtctttgg ttgtgttcca gtcccagtgt      360
ggtcagagtt catgtgtgag ctaaaaaaag ctactagtat tatgtaagta ctgcatgacc     420
catcatgact gttgacagct tgaactttgt gtcctattgt caccc                     465

<210> SEQ ID NO 2
<211> LENGTH: 222
<212> TYPE: DNA
<213> ORGANISM: Hordeum vulgare

<400> SEQUENCE: 2
atgatcgagg tggtgctcaa cgaccgcctg gggaagaagg tgcgcgtcaa gtgcaacgag      60
```

```
gacgacacca tcggcgacct caagaagctc gtggcggcgc agaccgggac cagggccgag    120
aagatccgca tccagaagtg gtacaccatc tacaaggacc acatcaccct tggcgactac    180
gagatccacg atgggatggg cctcgagctc tactacaact ag                       222
```

<210> SEQ ID NO 3
<211> LENGTH: 222
<212> TYPE: DNA
<213> ORGANISM: Oryza sativa indica

<400> SEQUENCE: 3

```
atgatcgagg tggtgctcaa cgaccggctg gggaagaagg tgcgcgtcaa gtgcaacgag    60
gacgacacca tcggcgacct gaagaagctg gtggcggcgc agacggggac gcgcgccgag    120
aagatccgca tccagaagtg gtacaacatc tacaaggacc acatcaccct cgccgactac    180
gagatccacg acgggatggg cctcgagctc tactacgact ag                       222
```

<210> SEQ ID NO 4
<211> LENGTH: 222
<212> TYPE: DNA
<213> ORGANISM: Oryza sativa japonica

<400> SEQUENCE: 4

```
atgatcgagg tggtgctcaa cgaccggctg gggaagaagg tgcgcgtcaa gtgcaacgag    60
gacgacacca tcggcgacct gaagaagctg gtggcggcgc agacggggac gcgcgccgag    120
aagatccgca tccagaagtg gtacaacatc tacaaggacc acatcaccct cgccgactac    180
gagatccacg acgggatggg cctcgagctc tactacgact ag                       222
```

<210> SEQ ID NO 5
<211> LENGTH: 222
<212> TYPE: DNA
<213> ORGANISM: Arabidopsis thaliana

<400> SEQUENCE: 5

```
atgatcgagg tggttctcaa cgatcgttta gggaaaaaag ttagggtgaa gtgtaacgat    60
gatgacacga tcggtgatct gaagaagctt gtcgcggcac aaaccggaac acgagccgag    120
aagatcagaa ttcagaagtg gtacaacatc tacaaggatc acatcactct caaggactat    180
gagatccatg acggcatggg tcttgagctt tactacaact ag                       222
```

<210> SEQ ID NO 6
<211> LENGTH: 222
<212> TYPE: DNA
<213> ORGANISM: Populus trichocarpa

<400> SEQUENCE: 6

```
atgttggagg tggtgttgaa cgatcgtttg ggaaagaaag tgagagtgaa gtgcaacgac    60
gacgacacga tcggcgacct caagaagctc gtggcggccc agaccggtac ccgagctgag    120
aagatccgga tccagaagtg gtacaacatc tataaagacc atattaccct caaggattac    180
gagattcatg atggcatggg cctcgagctc tactacaact ag                       222
```

<210> SEQ ID NO 7
<211> LENGTH: 222
<212> TYPE: DNA
<213> ORGANISM: Picea sitchensis

<400> SEQUENCE: 7

```
atgatcgagg tggtgctcaa cgatcggctg gggaagaagg ttcgggtgaa atgcaacgag    60
```

```
gatgcacacca tcggcgacct caagaagctc gtcgctgctc agactggaac ccgccccgat    120
aagatacgaa tccagaaatg gtacaacatc tacaaggatc acatcaccct gaaagactac    180
gaaatccatg atggcatggg tcttgaactt tattataact ag                       222
```

<210> SEQ ID NO 8
<211> LENGTH: 222
<212> TYPE: DNA
<213> ORGANISM: Physcomitrella patens

<400> SEQUENCE: 8

```
atgattgagg tggtgcttaa cgataggttg gggaagaagg tacgtgtgaa gtgcaacgaa     60
gatgatacaa ttggggatct caagaagctg gtagctgctc aaacaggaac gcgacctgag    120
aagattcgca tccagaagtg gtataccata tataaggatc acatcacttt gagtgattac    180
gaaattcatg atggcatggg actggagctc tactacaatt aa                       222
```

<210> SEQ ID NO 9
<211> LENGTH: 222
<212> TYPE: DNA
<213> ORGANISM: Ostreococcus lucimarinus

<400> SEQUENCE: 9

```
atgatcgaga tcacgctgaa cgaccgactc gggaagaaga tacgcgtcaa gtgcaacgag     60
gacgacacca tcggtgattt aaagaaactc gtcgccgcgc agacggggac gcggccggag    120
aagatacgga tacagaagtg gtacacgatt tataaggatc acatcacgct ggacgattac    180
gagattcacg acgggatgaa tctggagctg tactttaact ag                       222
```

<210> SEQ ID NO 10
<211> LENGTH: 73
<212> TYPE: PRT
<213> ORGANISM: Lolium perenne

<400> SEQUENCE: 10

```
Met Ile Glu Val Val Leu Asn Asp Arg Leu Gly Lys Lys Val Arg Val
1               5                   10                  15

Lys Cys Asn Glu Asp Asp Thr Ile Gly Asp Leu Lys Lys Leu Val Ala
                20                  25                  30

Ala Gln Thr Gly Thr Arg Pro Glu Lys Ile Arg Ile Gln Lys Trp Tyr
            35                  40                  45

Thr Ile Tyr Lys Asp His Ile Thr Leu Gly Asp Tyr Glu Ile His Asp
        50                  55                  60

Gly Met Gly Leu Glu Leu Tyr Tyr Asn
65                  70
```

<210> SEQ ID NO 11
<211> LENGTH: 73
<212> TYPE: PRT
<213> ORGANISM: Hordeum vulgare

<400> SEQUENCE: 11

```
Met Ile Glu Val Val Leu Asn Asp Arg Leu Gly Lys Lys Val Arg Val
1               5                   10                  15

Lys Cys Asn Glu Asp Asp Thr Ile Gly Asp Leu Lys Lys Leu Val Ala
                20                  25                  30

Ala Gln Thr Gly Thr Arg Ala Glu Lys Ile Arg Ile Gln Lys Trp Tyr
            35                  40                  45
```

-continued

Thr Ile Tyr Lys Asp His Ile Thr Leu Gly Asp Tyr Glu Ile His Asp
 50                  55                  60

Gly Met Gly Leu Glu Leu Tyr Tyr Asn
 65                  70

<210> SEQ ID NO 12
<211> LENGTH: 73
<212> TYPE: PRT
<213> ORGANISM: Oryza sativa indica

<400> SEQUENCE: 12

Met Ile Glu Val Val Leu Asn Asp Arg Leu Gly Lys Lys Val Arg Val
 1               5                   10                  15

Lys Cys Asn Glu Asp Asp Thr Ile Gly Asp Leu Lys Lys Leu Val Ala
                20                  25                  30

Ala Gln Thr Gly Thr Arg Ala Glu Lys Ile Arg Ile Gln Lys Trp Tyr
            35                  40                  45

Asn Ile Tyr Lys Asp His Ile Thr Leu Ala Asp Tyr Glu Ile His Asp
 50                  55                  60

Gly Met Gly Leu Glu Leu Tyr Tyr Asp
 65                  70

<210> SEQ ID NO 13
<211> LENGTH: 73
<212> TYPE: PRT
<213> ORGANISM: Oryza sativa japonica

<400> SEQUENCE: 13

Met Ile Glu Val Val Leu Asn Asp Arg Leu Gly Lys Lys Val Arg Val
 1               5                   10                  15

Lys Cys Asn Glu Asp Asp Thr Ile Gly Asp Leu Lys Lys Leu Val Ala
                20                  25                  30

Ala Gln Thr Gly Thr Arg Ala Glu Lys Ile Arg Ile Gln Lys Trp Tyr
            35                  40                  45

Asn Ile Tyr Lys Asp His Ile Thr Leu Ala Asp Tyr Glu Ile His Asp
 50                  55                  60

Gly Met Gly Leu Glu Leu Tyr Tyr Asp
 65                  70

<210> SEQ ID NO 14
<211> LENGTH: 73
<212> TYPE: PRT
<213> ORGANISM: Arabidopsis thaliana

<400> SEQUENCE: 14

Met Ile Glu Val Val Leu Asn Asp Arg Leu Gly Lys Lys Val Arg Val
 1               5                   10                  15

Lys Cys Asn Asp Asp Asp Thr Ile Gly Asp Leu Lys Lys Leu Val Ala
                20                  25                  30

Ala Gln Thr Gly Thr Arg Ala Glu Lys Ile Arg Ile Gln Lys Trp Tyr
            35                  40                  45

Asn Ile Tyr Lys Asp His Ile Thr Leu Lys Asp Tyr Glu Ile His Asp
 50                  55                  60

Gly Met Gly Leu Glu Leu Tyr Tyr Asn
 65                  70

<210> SEQ ID NO 15
<211> LENGTH: 73
<212> TYPE: PRT

<213> ORGANISM: Populus trichocarpa

<400> SEQUENCE: 15

Met Leu Glu Val Val Leu Asn Asp Arg Leu Gly Lys Lys Val Arg Val
1               5                   10                  15

Lys Cys Asn Asp Asp Asp Thr Ile Gly Asp Leu Lys Lys Leu Val Ala
                20                  25                  30

Ala Gln Thr Gly Thr Arg Ala Glu Lys Ile Arg Ile Gln Lys Trp Tyr
            35                  40                  45

Asn Ile Tyr Lys Asp His Ile Thr Leu Lys Asp Tyr Glu Ile His Asp
    50                  55                  60

Gly Met Gly Leu Glu Leu Tyr Tyr Asn
65                  70

<210> SEQ ID NO 16
<211> LENGTH: 73
<212> TYPE: PRT
<213> ORGANISM: Picea sitchensis

<400> SEQUENCE: 16

Met Ile Glu Val Val Leu Asn Asp Arg Leu Gly Lys Lys Val Arg Val
1               5                   10                  15

Lys Cys Asn Glu Asp Asp Thr Ile Gly Asp Leu Lys Lys Leu Val Ala
                20                  25                  30

Ala Gln Thr Gly Thr Arg Pro Asp Lys Ile Arg Ile Gln Lys Trp Tyr
            35                  40                  45

Asn Ile Tyr Lys Asp His Ile Thr Leu Lys Asp Tyr Glu Ile His Asp
    50                  55                  60

Gly Met Gly Leu Glu Leu Tyr Tyr Asn
65                  70

<210> SEQ ID NO 17
<211> LENGTH: 73
<212> TYPE: PRT
<213> ORGANISM: Physcomitrella patens

<400> SEQUENCE: 17

Met Ile Glu Val Val Leu Asn Asp Arg Leu Gly Lys Lys Val Arg Val
1               5                   10                  15

Lys Cys Asn Glu Asp Asp Thr Ile Gly Asp Leu Lys Lys Leu Val Ala
                20                  25                  30

Ala Gln Thr Gly Thr Arg Pro Glu Lys Ile Arg Ile Gln Lys Trp Tyr
            35                  40                  45

Thr Ile Tyr Lys Asp His Ile Thr Leu Ser Asp Tyr Glu Ile His Asp
    50                  55                  60

Gly Met Gly Leu Glu Leu Tyr Tyr Asn
65                  70

<210> SEQ ID NO 18
<211> LENGTH: 73
<212> TYPE: PRT
<213> ORGANISM: Ostreococcus lucimarinus

<400> SEQUENCE: 18

Met Ile Glu Ile Thr Leu Asn Asp Arg Leu Gly Lys Lys Ile Arg Val
1               5                   10                  15

Lys Cys Asn Glu Asp Asp Thr Ile Gly Asp Leu Lys Lys Leu Val Ala
                20                  25                  30

```
Ala Gln Thr Gly Thr Arg Pro Glu Lys Ile Arg Ile Gln Lys Trp Tyr
        35                  40                  45

Thr Ile Tyr Lys Asp His Ile Thr Leu Asp Asp Tyr Glu Ile His Asp
 50                  55                  60

Gly Met Asn Leu Glu Leu Tyr Phe Asn
 65                  70

<210> SEQ ID NO 19
<211> LENGTH: 18
<212> TYPE: PRT
<213> ORGANISM: Artificial
<220> FEATURE:
<223> OTHER INFORMATION: consensus

<400> SEQUENCE: 19

Asp Asp Thr Ile Gly Asp Leu Lys Lys Leu Val Ala Ala Gln Thr Gly
 1               5                  10                  15

Thr Arg

<210> SEQ ID NO 20
<211> LENGTH: 17
<212> TYPE: PRT
<213> ORGANISM: Artificial
<220> FEATURE:
<223> OTHER INFORMATION: consensus

<400> SEQUENCE: 20

Glu Val Val Leu Asn Asp Arg Leu Gly Lys Lys Val Arg Val Lys Cys
 1               5                  10                  15

Asn

<210> SEQ ID NO 21
<211> LENGTH: 38
<212> TYPE: PRT
<213> ORGANISM: Artificial
<220> FEATURE:
<223> OTHER INFORMATION: consensus

<400> SEQUENCE: 21

Met Ile Glu Val Val Leu Asn Asp Arg Leu Gly Lys Lys Val Arg Val
 1               5                  10                  15

Lys Cys Asn Glu Asp Asp Thr Ile Gly Asp Leu Lys Lys Leu Val Ala
                20                  25                  30

Ala Gln Thr Gly Thr Arg
        35

<210> SEQ ID NO 22
<211> LENGTH: 71
<212> TYPE: PRT
<213> ORGANISM: Artificial
<220> FEATURE:
<223> OTHER INFORMATION: consensus

<400> SEQUENCE: 22

Glu Val Val Leu Asn Asp Arg Leu Gly Lys Lys Val Arg Val Lys Cys
 1               5                  10                  15

Asn Asp Asp Asp Thr Ile Gly Asp Leu Lys Lys Leu Val Ala Ala Gln
                20                  25                  30

Thr Gly Thr Arg Ala Glu Lys Ile Arg Ile Gln Lys Trp Tyr Asn Ile
        35                  40                  45

Tyr Lys Asp His Ile Thr Leu Lys Asp Tyr Glu Ile His Asp Gly Met
 50                  55                  60
```

Gly Leu Glu Leu Tyr Tyr Asn
65                    70

<210> SEQ ID NO 23
<211> LENGTH: 10449
<212> TYPE: DNA
<213> ORGANISM: Artificial
<220> FEATURE:
<223> OTHER INFORMATION: vector

<400> SEQUENCE: 23

```
ggaattcgat atcaagcttg gcactggccg tcgttttaca acgtcgtgac tgggaaaacc     60
ctggcgttac ccaacttaat cgccttgcag cacatccccc tttcgccagc tggcgtaata    120
gcgaagaggc ccgcaccgat cgcccttccc aacagttgcg cagcctgaat ggcgaatgct    180
agagcagctt gagcttggat cagattgtcg tttcccgcct tcagtttaaa ctatcagtgt    240
ttgacaggat atattggcgg gtaaacctaa gagaaaagag cgtttattag aataacggat    300
atttaaaagg gcgtgaaaag gtttatccgt tcgtccattt gtatgtgcat gccaaccaca    360
gggttcccct cgggatcaaa gtactttgat ccaaccccct cgctgctata gtgcagtcgg    420
cttctgacgt tcagtgcagc cgtcttctga aacgacatg tcgcacaagt cctaagttac     480
gcgacaggct gccgccctgc cctttcctg gcgttttctt gtcgcgtgtt ttagtcgcat      540
aaagtagaat acttgcgact agaaccggag acattacgcc atgaacaaga gcgccgccgc    600
tggcctgctg ggctatgccc gcgtcagcac cgacgaccag gacttgacca accaacgggc    660
cgaactgcac gcggccggct gcaccaagct gttttccgag aagatcaccg gcaccaggcg    720
cgaccgcccg gagctggcca ggatgcttga ccacctacgc cctggcgacg ttgtgacagt    780
gaccaggcta gaccgcctgg cccgcagcac ccgcgaccta ctggacattg ccgagcgcat    840
ccaggaggcc ggcgcgggcc tgcgtagcct ggcagagccg tgggccgaca ccaccacgcc    900
ggccggccgc atggtgttga ccgtgttcgc cggcattgcc gagttcgagc gttccctaat    960
catcgaccgc acccggagcg ggcgcgaggc cgccaaggcc cgaggcgtga agtttggccc   1020
cgccctacc ctcacccgg cacagatcgc gcacgcccgc gagctgatcg accaggaagg    1080
ccgcaccgtg aaagaggcgg ctgcactgct tggcgtgcat cgctcgaccc tgtaccgcgc   1140
acttgagcgc agcgaggaag tgacgcccac cgaggccagg cggcgcggtg ccttccgtga   1200
ggacgcattg accgaggccg acgccctggc ggccgccgag aatgaacgcc aagaggaaca   1260
agcatgaaac cgcaccagga cggccaggac gaaccgtttt tcattaccga agagatcgag   1320
gcggagatga tcgcggccgg gtacgtgttc gagccgcccg cgcacgtctc aaccgtgcgg   1380
ctgcatgaaa tcctggccgg tttgtctgat gccaagctgg cggcctggcc ggccagcttg   1440
gccgctgaag aaaccgagcg ccgccgtcta aaaaggtgat gtgtatttga gtaaaacagc   1500
ttgcgtcatg cggtcgctgc gtatatgatg cgatgagtaa ataaacaaat acgcaagggg   1560
aacgcatgaa ggttatcgct gtacttaacc agaaaggcgg gtcaggcaag acgaccatcg   1620
caacccatct agcccgcgcc ctgcaactcg ccggggccga tgttctgtta gtcgattccg   1680
atccccaggg cagtgcccgc gattgggcgg ccgtgcggga agatcaaccg ctaaccgttg   1740
tcggcatcga ccgcccgacg attgaccgcg acgtgaaggc catcggccgg cgcgacttcg   1800
tagtgatcga cggagcgccc caggcggcgg acttggctgt gtccgcgatc aaggcagccg   1860
acttcgtgct gattccggtg cagccaagcc cttacgacat atgggccacc gccgacctgg   1920
tggagctggt taagcagcgc attgaggtca cggatggaag gctacaagcg gcctttgtcg   1980
```

```
tgtcgcgggc gatcaaaggc acgcgcatcg gcggtgaggt tgccgaggcg ctggccgggt    2040
acgagctgcc cattcttgag tcccgtatca cgcagcgcgt gagctaccca ggcactgccg    2100
ccgccggcac aaccgttctt gaatcagaac ccgagggcga cgctgcccgc gaggtccagg    2160
cgctggccgc tgaaattaaa tcaaaactca tttgagttaa tgaggtaaag agaaaatgag    2220
caaaagcaca aacacgctaa gtgccggccg tccgagcgca cgcagcagca aggctgcaac    2280
gttggcagcc ctggcagaca cgccagccat gaagcgggtc aactttcagt tgccggcgga    2340
ggatcacacc aagctgaaga tgtacgcggt acgccaaggc aagaccatta ccgagctgct    2400
atctgaatac atcgcgcagc taccagagta aatgagcaaa tgaataaatg agtagatgaa    2460
ttttagcggc taaggaggcg gcatggaaaa tcaagaaca accaggcacc gacgccgtgg    2520
aatgccccat gtgtggagga acgggcggtt ggccaggcgt aagcggctgg gttgtctgcc    2580
ggccctgcaa tggcactgga accccaagc ccgaggaatc ggcgtgacgg tcgcaaacca    2640 tccggccccgg tacaaatcgg cgcggcgctg ggtgatgacc tggtggagaa gttgaaggcc    2700
gcgcaggccg cccagcggca acgcatcgag gcagaagcac gccccggtga atcgtggcaa    2760
gcggccgctg atcgaatccg caaagaatcc cggcaaccgc cggcagccgg tgcgccgtcg    2820
attaggaagc cgcccaaggg cgacgagcaa ccagatttt tcgttccgat gctctatgac    2880
gtgggcaccc cgcatagtcg cagcatcatg gacgtggccg ttttccgtct gtcgaagcgt    2940
gaccgacgag ctggcgaggt gatccgctac gagcttccag acgggcacgt agaggtttcc    3000
gcagggccgg ccggcatggc cagtgtgtgg gattacgacc tggtactgat ggcggttttcc    3060 catctaaccg aatccatgaa ccgataccgg gaagggaagg gagacaagcc cggccgcgtg    3120
ttccgtccac acgttgcgga cgtactcaag ttctgccggc gagccgatgg cggaaagcag    3180
aaagacgacc tggtagaaac ctgcattcgg ttaaacacca cgcacgttgc catgcagcgt    3240
acgaagaagg ccaagaacgg ccgcctggtg acggtatccg agggtgaagc cttgattagc    3300
cgctacaaga tcgtaaagag cgaaaccggg cggccggagt acatcgagat cgagctagct    3360
gattggatgt accgcgagat cacagaaggc aagaacccgg acgtgctgac ggttcacccc    3420
gattactttt tgatcgatcc cggcatcggc cgttttctct accgcctggc acgccgcgcc    3480
gcaggcaagg cagaagccag atggttgttc aagacgatct acgaacgcag tggcagcgcc    3540
ggagagttca agaagttctg tttcaccgtg cgcaagctga tcgggtcaaa tgacctgccg    3600
gagtacgatt tgaaggagga ggcggggcag gctggcccga tcctagtcat gcgctaccgc    3660
aacctgatcg agggcgaagc atccgccggt tcctaatgta cggagcagat gctagggcaa    3720
attgccctag caggggaaaa aggtcgaaaa ggtctctttc ctgtggatag cacgtacatt    3780
gggaacccaa agccgtacat tgggaaccgg aacccgtaca ttgggaaccc aaagccgtac    3840
attgggaacc ggtcacacat gtaagtgact gatataaaag agaaaaaagg cgatttttcc    3900
gcctaaaact ctttaaaact tattaaaact cttaaaaccc gcctggcctg tgcataactg    3960
tctggccagc gcacagccga agagctgcaa aaagcgccta cccttcggtc gctgcgctcc    4020
ctacgccccg ccgcttcgcg tcggcctatc gcggccgctg ccgctcaaa aatggctggc    4080 ctacggccag gcaatctacc agggcgcgga caagccgcgc cgtcgccact cgaccgccgg    4140
cgcccacatc aaggcaccct gcctcgcgcg tttcggtgat gacggtgaaa acctctgaca    4200
catgcagctc ccggagacgg tcacagcttg tctgtaagcg gatgccggga gcagacaagc    4260
ccgtcagggc gcgtcagcgg gtgttggcgg gtgtcggggc gcagccatga cccagtcacg    4320
```

```
tagcgatagc ggagtgtata ctggcttaac tatgcggcat cagagcagat tgtactgaga    4380
gtgcaccata tgcggtgtga aataccgcac agatgcgtaa ggagaaaata ccgcatcagg    4440
cgctcttccg cttcctcgct cactgactcg ctgcgctcgg tcgttcggct gcggcgagcg    4500
gtatcagctc actcaaaggc ggtaatacgg ttatccacag aatcagggga taacgcagga    4560
aagaacatgt gagcaaaagg ccagcaaaag gccaggaacc gtaaaaaggc cgcgttgctg    4620
gcgtttttcc ataggctccg cccccctgac gagcatcaca aaaatcgacg ctcaagtcag    4680
aggtggcgaa acccgacagg actataaaga taccaggcgt ttccccctgg aagctccctc    4740
gtgcgctctc ctgttccgac cctgccgctt accggatacc tgtccgcctt tctcccttcg    4800
ggaagcgtgg cgctttctca tagctcacgc tgtaggtatc tcagttcggt gtaggtcgtt    4860
cgctccaagc tgggctgtgt gcacgaaccc cccgttcagc ccgaccgctg cgccttatcc    4920
ggtaactatc gtcttgagtc caacccggta agacacgact tatcgccact ggcagcagcc    4980
actggtaaca ggattagcag agcgaggtat gtaggcggtg ctacagagtt cttgaagtgg    5040
tggcctaact acggctacac tagaaggaca gtatttggta tctgcgctct gctgaagcca    5100
gttaccttcg gaaaaagagt tggtagctct tgatccggca aacaaaccac cgctggtagc    5160
ggtggttttt ttgtttgcaa gcagcagatt acgcgcagaa aaaaaggatc tcaagaagat    5220
cctttgatct tttctacggg gtctgacgct cagtggaacg aaaactcacg ttaagggatt    5280
ttggtcatgc attctaggta ctaaaacaat tcatccagta aaatataata ttttatttc    5340
tcccaatcag gcttgatccc cagtaagtca aaaaatagct cgacatactg ttcttccccg    5400
atatcctccc tgatcgaccg gacgcagaag gcaatgtcat accacttgtc cgccctgccg    5460
cttctcccaa gatcaataaa gccacttact tgccatcttt cacaaagat gttgctgtct    5520
cccaggtcgc cgtgggaaaa gacaagttcc tcttcgggct tttccgtctt taaaaaatca    5580
tacagctcgc gcggatcttt aaatggagtg tcttcttccc agttttcgca atccacatcg    5640
gccagatcgt tattcagtaa gtaatccaat tcggctaagc ggctgtctaa gctattcgta    5700
tagggacaat ccgatatgtc gatggagtga aagagcctga tgcactccgc atacagctcg    5760
ataatctttt cagggctttg ttcatcttca tactcttccg agcaaaggac gccatcggcc    5820
tcactcatga gcagattgct ccagccatca tgccgttcaa agtgcaggac ctttggaaca    5880
ggcagctttc cttccagcca tagcatcatg tccttttccc gttccacatc ataggtggtc    5940
cctttatacc ggctgtccgt cattttaaa tataggtttt cattttctcc caccagctta    6000
tataccttag caggagacat tccttccgta tcttttacgc agcggtattt ttcgatcagt    6060
ttttcaatt ccggtgatat tctcatttta gccatttatt atttccttcc tcttttctac    6120
agtatttaaa gataccccaa gaagctaatt ataacaagac gaactccaat tcactgttcc    6180
ttgcattcta aaaccttaaa taccagaaaa cagcttttc aaagttgttt tcaaagttgg    6240
cgtataacat agtatcgacg gagccgattt tgaaaccgcg gtgatcacag gcagcaacgc    6300
tctgtcatcg ttacaatcaa catgctaccc tccgcgagat catccgtgtt tcaaacccgg    6360
cagcttagtt gccgttcttc cgaatagcat cggtaacatg agcaaagtct gccgccttac    6420
aacggctctc ccgctgacgc cgtcccggac tgatgggctg cctgtatcga gtggtgattt    6480
tgtgccgagc tgccggtcgg ggagctgttg gctggctggt ggcaggatat attgtggtgt    6540
aaacaaattg acgcttagac aacttaataa cacattgcgg acgttttaa tgtactgaat    6600
taacgccgaa ttaattcggg ggatctggat tttagtactg gattttggtt ttaggaatta    6660
gaaattttat tgatagaagt attttacaaa tacaaataca tactaagggt ttcttatatg    6720
```

```
ctcaacacat gagcgaaacc ctataggaac cctaattccc ttatctggga actactcaca    6780
cattattatg gagaaactcg agcttgtcga tcgacagatc cggtcggcat ctactctatt    6840
tctttgccct cggacgagtg ctggggcgtc ggtttccact atcggcgagt acttctacac    6900
agccatcggt ccagacggcc gcgcttctgc gggcgatttg tgtacgcccg acagtcccgg    6960
ctccggatcg gacgattgcg tcgcatcgac cctgcgccca agctgcatca tcgaaattgc    7020
cgtcaaccaa gctctgatag agttggtcaa gaccaatgcg gagcatatac gcccggagtc    7080
gtggcgatcc tgcaagctcc ggatgcctcc gctcgaagta gcgcgtctgc tgctccatac    7140
aagccaacca cggcctccag aagaagatgt tggcgacctc gtattgggaa tccccgaaca    7200
tcgcctcgct ccagtcaatg accgctgtta tgcggccatt gtccgtcagg acattgttgg    7260
agccgaaatc cgcgtgcacg aggtgccgga cttcggggca gtcctcggcc caaagcatca    7320
gctcatcgag agcctgcgcg acggacgcac tgacggtgtc gtccatcaca gtttgccagt    7380
gatacacatg gggatcagca atcgcgcata tgaaatcacg ccatgtagtg tattgaccga    7440
ttccttgcgg tccgaatggg ccgaacccgc tcgtctggct aagatcggcc gcagcgatcg    7500
catccatagc ctccgcgacc ggttgtagaa cagcgggcag ttcggtttca ggcaggtctt    7560
gcaacgtgac accctgtgca cggcgggaga tgcaataggt caggctctcg ctaaactccc    7620
caatgtcaag cacttccgga atcgggagcg cggccgatgc aaagtgccga taaacataac    7680
gatctttgta gaaaccatcg gcgcagctat ttacccgcag gacatatcca cgccctccta    7740
catcgaagct gaaagcacga gattcttcgc cctccgagag ctgcatcagg tcggagacgc    7800
tgtcgaactt ttcgatcaga aacttctcga cagacgtcgc ggtgagttca ggcttttttca    7860 tatctcattg ccccccccgga tctgcgaaag ctcgagagag atagatttgt agagagagac    7920
tggtgatttc agcgtgtcct ctccaaatga aatgaacttc cttatataga ggaaggtctt    7980
gcgaaggata gtgggattgt gcgtcatccc ttacgtcagt ggagatatca catcaatcca    8040
cttgctttga agacgtggtt ggaacgtctt cttttttccac gatgctcctc gtgggtgggg    8100
gtccatcttt gggaccactg tcggcagagg catcttgaac gatagccttt cctttatcgc    8160
aatgatggca tttgtaggtg ccaccttcct ttttctactgt ccttttgatg aagtgacaga    8220
tagctgggca atggaatccg aggaggtttc ccgatattac cctttgttga aaagtctcaa    8280
tagccctttg gtcttctgag actgtatctt tgatattctt ggagtagacg agagtgtcgt    8340
gctccaccat gttatcacat caatccactt gctttgaaga cgtggttgga acgtcttctt    8400 tttcacgat gctcctcgtg ggtggggggtc catctttggg accactgtcg gcagaggcat    8460
cttgaacgat agccttcct ttatcgcaat gatggcattt gtaggtgcca ccttcctttt    8520
ctactgtcct tttgatgaag tgacagatag ctgggcaatg gaatccgagg aggtttcccg    8580
atattaccct tgttgaaaa gtctcaatag cccttggtc ttctgagact gtatctttga    8640
tattcttgga gtagacgaga gtgtcgtgct ccaccatgtt ggcaagctgc tctagccaat    8700
acgcaaaccg cctctccccg cgcgttggcc gattcattaa tgcagctggc acgacaggtt    8760
tcccgactgg aaagcgggca gtgagcgcaa cgcaattaat gtgagttagc tcactcatta    8820
ggcaccccag gctttacact ttatgcttcc ggctcgtatg ttgtgtggaa ttgtgagcgg    8880
ataacaattt cacacaggaa acagctatga ccatgattac gaattcccctt aattaataag    8940 agcagcttgc caacatggtg gagcacgaca ctctcgtcta ctccaagaat atcaaagata    9000
cagtctcaga agaccaaagg gctattgaga cttttcaaca aagggtaata tcgggaaacc    9060
```

-continued

| | |
|---|---|
| tcctcggatt ccattgccca gctatctgtc acttcatcaa aaggacagta gaaaaggaag | 9120 |
| gtggcaccta caaatgccat cattgcgata aaggaaaggc tatcgttcaa gatgcctctg | 9180 |
| ccgacagtgg tcccaaagat ggaccccac ccacgaggag catcgtggaa aaagaagacg | 9240 |
| ttccaaccac gtcttcaaag caagtggatt gatgtgaaca tggtggagca cgacactctc | 9300 |
| gtctactcca agaatatcaa agatacagtc tcagaaggcc aaagggctat tgagactttt | 9360 |
| caacaaaggg taatatcggg aaacctcctc ggattccatt gcccagctat ctgtcacttc | 9420 |
| atcaaaagga cagtagaaaa ggaaggtggc acctacaaat gccatcattg cgataaagga | 9480 |
| aaggctatcg ttcaagatgc tctgccgaca gtggtcccaa agatggaccc ccacccacga | 9540 |
| ggagcatcgt ggaaaaagaa gacgttccaa ccacgtcttc aaagcaagtg gattgatgtg | 9600 |
| atatctccac tgacgtaagg gatgacgcac aatcccacta tccttcgcaa gacccttcct | 9660 |
| ctatataagg aagttcattt catttggaga ggacacgctg aaatcaccag tctctctcta | 9720 |
| caaatctatc tctctccatt aggaagagct agggtttggt cgagaggagg ccggcggccg | 9780 |
| ggcgatcgac cgaagatgat cgaggtggtg ctcaacgacc gtctgggaa aaggtgcgc | 9840 |
| gtcaagtgca acgaggacga caccatcggc gacctcaaga agctcgtcgc ggcgcagacc | 9900 |
| gggaccaggc ccgagaagat ccgcatccag aagtggtaca ccatctacaa ggaccacatc | 9960 |
| accctcggcg actacgagat ccacgacgga atgggactcg agctctacta caactagccc | 10020 |
| attcaatctc cccagccatg ttggtatgca tcccctagc catccctaga tgatgtcttt | 10080 |
| ggttgtgttc cagtcccagt gtggtcagag ttcatgtgtg agctaaaaaa agctactagt | 10140 |
| attatgtaag tactgcatga cccatcatga ctgttgacag cttgaacttt gtgtcctatt | 10200 |
| gtcacccggc ctggtttctc cataataatg tgtgagtagt tcccagataa gggaattagg | 10260 |
| gttcctatag ggtttcgctc atgtgttgag catataagaa acccttagta tgtatttgta | 10320 |
| tttgtaaaat acttctatca ataaaatttc taattcctaa aaccaaaatc cagtactaaa | 10380 |
| atccagatcc cccgaattaa ttcggcgtta attcagtatc ggcgcgcctt aattaaggcg | 10440 |
| cgccctgca | 10449 |

<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24
gtctcgacta cctcggcaac                      20

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
accgaacatg gagaacatgg                      20

<210> SEQ ID NO 26
<211> LENGTH: 21
<212> TYPE: DNA
<213> ORGANISM: Artificial
<220> FEATURE:
<223> OTHER INFORMATION: primer

```
<400> SEQUENCE: 26
aatacgaggt cgccaacatc t                                              21

<210> SEQ ID NO 27
<211> LENGTH: 23
<212> TYPE: DNA
<213> ORGANISM: Artificial
<220> FEATURE:
<223> OTHER INFORMATION: primer

<400> SEQUENCE: 27 aggaaccta attcccttat ctg                                             23

<210> SEQ ID NO 28
<211> LENGTH: 26
<212> TYPE: DNA
<213> ORGANISM: Artificial
<220> FEATURE:
<223> OTHER INFORMATION: primer

<400> SEQUENCE: 28
gaagagctag ggtttggtcg agagga                                         26

<210> SEQ ID NO 29
<211> LENGTH: 23
<212> TYPE: DNA
<213> ORGANISM: Artificial
<220> FEATURE:
<223> OTHER INFORMATION: primer

<400> SEQUENCE: 29
aggaacccta attcccttat ctg                                            23

<210> SEQ ID NO 30
<211> LENGTH: 21
<212> TYPE: DNA
<213> ORGANISM: Artificial
<220> FEATURE:
<223> OTHER INFORMATION: primer

<400> SEQUENCE: 30
aatacgaggt cgccaacatc t                                              21

<210> SEQ ID NO 31
<211> LENGTH: 23
<212> TYPE: DNA
<213> ORGANISM: Artificial
<220> FEATURE:
<223> OTHER INFORMATION: primer

<400> SEQUENCE: 31
aggaacccta attcccttat ctg                                            23

<210> SEQ ID NO 32
<211> LENGTH: 12
<212> TYPE: DNA
<213> ORGANISM: Artificial
<220> FEATURE:
<223> OTHER INFORMATION: Synthetic construct

<400> SEQUENCE: 32
gatctataga tc                                                        12

<210> SEQ ID NO 33
```

```
<211> LENGTH: 10
<212> TYPE: DNA
<213> ORGANISM: Artificial
<220> FEATURE:
<223> OTHER INFORMATION: SAGE tag

<400> SEQUENCE: 33
actgttgaca                                                                10

<210> SEQ ID NO 34
<211> LENGTH: 17
<212> TYPE: DNA
<213> ORGANISM: Artificial
<220> FEATURE:
<223> OTHER INFORMATION: SAGE tag

<400> SEQUENCE: 34
actgttgaca gcttgaa                                                        17
```

METHODS AND COMPOSITIONS FOR PLANT IMPROVEMENT

CROSS-REFERENCE TO RELATED APPLICATIONS

This application is a National Stage Application filed under 35 U.S.C. §371 of PCT Application No. PCT/NZ2009/000090, filed on May 26, 2009 and published in English on Dec. 3, 2009 as WO 2009/145645, which claims priority to U.S. Provisional application 61/056,583, filed on May 28, 2008, all of which are incorporated by reference in their entireties to the extent there is no inconsistency with the present disclosure.

TECHNICAL FIELD

The present invention relates to compositions and methods for producing plants with improved stress tolerance.

BACKGROUND ART

Environmental abiotic stresses, including drought stress, cold stress, freezing stress, heat stress and salinity stress are major factors limiting plant growth and productivity. Crop losses and reduction in yield of major crops including maize, wheat and rice caused by such stresses represent significant economic issues and also lead to food shortages in several underdeveloped countries.

The development of stress tolerant plants has the potential to reduce or solve at least some of these problems. The use of traditional plant breeding strategies to produce new lines of plants that exhibit tolerance to these types of stresses has been slow. Lack of sufficient germplasm resources and incompatibility between distantly related plant species, present significant problems in conventional breeding. Further, the cellular processes leading to tolerance to such stresses are complex and involve multiple mechanisms of cellular adaptation and numerous metabolic pathways. This limits the success of both traditional breeding and that of genetic engineering approaches to development of stress tolerant plants. It would be beneficial to identify genes and proteins involved in controlling the complex processes leading to stress tolerance.

Regulators of gene expression, such as transcription factors, involved in controlling stress tolerance may be particularly useful in genetic engineering of plants, as a single gene may control a whole cascade of genes leading to the tolerance phenotype. Furthermore, there is sometimes commonality in many aspects of the different types of stress tolerant responses referred above. For example, genes that increase tolerance to cold or salt may also improve drought stress tolerance. This has been demonstrated in the case of the transcription factor At CBF/DREB 1 (Kasuga et al., 1999 Nature Biotech 17: 287-91) and the vacuolar pyrophosphatase AVP1 (Gaxiola et al., 2001 PNAS 98:11444-19).

Whilst some potentially useful genes have been identified, the identification and cloning of plant genes that confer tolerance to stress remains fragmented and incomplete. Although it is assumed that stress induced proteins may have a role in stress tolerance, evidence is still lacking and the function of many such stress responsive genes is unknown.

The hot and dry weather conditions in New Zealand and other countries in the summer period can have significant effect upon the yield of ryegrass. This is invariably during the dairy milking season and therefore has real effects on cost of dairy production through either reduced milk yield or the use of supplementary feeds and/or irrigation systems.

It would be beneficial to identify genes which have the capacity to confer stress tolerance in stress susceptible plant species. The development of stress tolerant crops will provide many advantages such as increasing yield and producing plants that may be cultivated in previously unsuitable environmental conditions. Thus, there exists a need for compositions and methods for producing plants with improved stress tolerance relative to cultivated counterparts.

It is an object of the invention to provide improved compositions and methods for developing plant varieties with improved tolerance to at least one of the following stresses; drought, cold, freezing, heat and salinity, or at least to provide the public with a useful choice.

SUMMARY OF THE INVENTION

Polynucleotides

In one aspect the invention provides an isolated polynucleotide comprising the sequence of SEQ ID NO: 1 or a variant thereof, wherein the variant encodes a polypeptide capable of modulating in a plant tolerance to at least one environmental stress selected from drought, cold, freezing, heat and salinity.

In one embodiment the isolated polynucleotide comprises a sequence with at least 70% identity to the sequence of SEQ ID NO:1

In a further embodiment the isolated polynucleotide comprises the sequence of SEQ ID NO: 1.

In a further embodiment the isolated polynucleotide comprises a sequence with at least 70% identity to the coding sequence of SEQ ID NO:1

In a further embodiment the isolated polynucleotide comprises the coding sequence of SEQ ID NO: 1.

In a further embodiment the isolated polynucleotide comprises a sequence capable of hybridising under stringent conditions to the sequence of SEQ ID NO:1

In a further embodiment the isolated polynucleotide comprises a sequence capable of hybridising under stringent conditions to the coding sequence of SEQ ID NO:1

In one embodiment the variant comprises the sequence of any one of SEQ ID NO: 2 to 9.

In a further aspect the invention provides an isolated polynucleotide comprising a fragment, of at least 70 nucleotides in length, of a polynucleotide of the invention.

In one embodiment the environmental stress is drought.

In a further embodiment the environmental stress is cold.

In a further embodiment the environmental stress is freezing.

In a further embodiment the environmental stress is heat.

In a further embodiment the environmental stress is salinity.

In a further aspect the invention provides a genetic construct comprising a polynucleotide of the invention.

In one embodiment the genetic construct is an expression construct.

In a further aspect the invention provides a vector comprising a polynucleotide, genetic construct or expression construct of the invention.

In a further aspect the invention provides a host cell comprising a polynucleotide, genetic construct or expression construct of the invention.

In a further aspect the invention provides a host cell genetically modified to express a polynucleotide of the invention.

In preferred embodiments the host cell does not form part of a living human being.

In a further aspect the invention provides a plant cell comprising a genetic construct or the expression construct of the invention.

In a further aspect the invention provides a plant cell genetically modified to express a polynucleotide of the invention.

In a further aspect the invention provides a plant which comprises a plant cell of the invention.

Methods Using Polynucleotides

In a further aspect the invention provides a method of producing a plant with altered tolerance to at least one environmental stress selected from drought, cold, freezing heat and salinity, the method comprising transformation of a plant cell or plant with:
   a) a polynucleotide comprising the nucleotide sequence of SEQ ID NO:1, or a variant thereof, wherein the variant encodes a polypeptide capable of increasing tolerance to at least one environmental stress selected from drought, cold, freezing, heat and salinity;
   b) a polynucleotide comprising a fragment, of at least 15 nucleotides in length, of the polynucleotide of a); or
   c) a polynucleotide comprising a complement of the polynucleotide of a) or b)

The altered tolerance may be either increased or decreased tolerance.

Preferably the altered tolerance is increased tolerance.

Preferably the plant is transformed with a genetic construct or vector comprising the polynucleotide.

In one embodiment the environmental stress is drought.

In a further embodiment the environmental stress is cold.

In a further embodiment the environmental stress is freezing.

In a further embodiment the environmental stress is heat.

In a further embodiment the environmental stress is salinity.

In a further embodiment the variant comprises the sequence of any one of SEQ ID NO: 2 to 9.

In a further embodiment the polynucleotide of a) comprises the sequence of SEQ ID NO: 1.

Methods—Using Polynucleotides Encoding Polypeptides

In a further aspect the invention provides a method for producing a plant with altered tolerance to at least one environmental stress selected from drought, cold, freezing, heat and salinity, the method comprising transformation of a plant cell of plant with:
   a) a polynucleotide encoding of a polypeptide with the amino acid sequence of SEQ ID NO:10 or a variant of the polypeptide, wherein the variant is capable of increasing tolerance to at least one environmental stress selected from drought, cold, freezing, heat and salinity;
   b) a polynucleotide comprising a fragment, of at least 15 nucleotides in length, of the polynucleotide of a); or
   c) a polynucleotide comprising a complement of the polynucleotide of a) or b).

The altered tolerance may be either increased or decreased tolerance.

Preferably the altered tolerance is increased tolerance.

Preferably the plant is transformed with a genetic construct or vector comprising the polynucleotide.

In a further embodiment the polypeptide variant has at least 70% sequence identity to a polypeptide with the amino acid sequence of SEQ ID NO: 10.

In a further embodiment the polypeptide variant is from a Viridiplantae species and comprises the amino acid sequence of SEQ ID NO:19.

In a further embodiment the polypeptide variant is from a magnoliophyta (flowering plant) species and comprises the amino acid sequence of SEQ ID NO:20. Preferably the polypeptide variant of this embodiment also comprises the amino acid sequence of SEQ ID NO:19.

In a further embodiment the polypeptide variant is from a monocotyledonous plant species and comprises the amino acid sequence of SEQ ID NO:21.

In a further embodiment the polypeptide variant is from a dicotyledonous plant species and comprises the amino acid sequence of SEQ ID NO:22.

In a preferred embodiment the polypeptide variant comprises an amino acid sequence selected from any one of SEQ ID NO: 2-10.

In a more preferred embodiment the polynucleotide of a) encodes a polypeptide with the amino acid sequence of SEQ ID NO: 1.

In one embodiment the environmental stress is drought.

In a further embodiment the environmental stress is cold.

In a further embodiment the environmental stress is freezing.

In a further embodiment the environmental stress is heat.

In a further embodiment the environmental stress is salinity.

Methods—Selection

In a further aspect the invention provides a method for selecting a plant with increased tolerance to at least one environmental stress selected from drought, cold freezing, heat and salinity relative to suitable control plant, the method comprising testing of a plant for altered expression of a polynucleotide of the invention.

Plants

In a further aspect the invention provides a plant cell or plant produced by the method of the invention.

In a further aspect the invention provides a group, or population, of plants selected by the method of the invention.

Source of Polynucleotides of the Invention

The polynucleotides and polynucleotide variants of the invention may be derived from any species and/or may be produced synthetically or recombinantly.

In one embodiment the polynucleotide or variant, is derived from a plant species.

In a further embodiment the polynucleotide or variant, is derived from a gymnosperm plant species.

In a further embodiment the polynucleotide or variant, is derived from an angiosperm plant species.

In a further embodiment the polynucleotide or variant, is derived from a from dicotyledonous plant species.

In a further embodiment the polynucleotide or variant, is derived from a monocotyledonous plant species.

The recited polypeptides and polypeptide variants may be derived from all of the same sources as the polynucleotides and variants of the invention.

Source of Plant Cells and Plants of the Invention

The plant cells and plants, of the invention may be derived from any species.

In one embodiment the plant cell or plant, is derived from a gymnosperm plant species.

In a further embodiment the plant cell or plant, is derived from an angiosperm plant species.

In a further embodiment the plant cell or plant, is derived from a from dicotyledonous plant species.

In a further embodiment the plant cell or plant, is derived from a monocotyledonous plant species.

Preferred dicotyledonous genera include: *Amygdalus, Anacardium, Anemone, Arachis, Brassica, Cajanus, Cannabis, Carthamus, Carya, Ceiba, Cicer, Claytonia, Coriandrum, Coronilla, Corydalis, Crotalaria, Cyclamen, Dentaria, Dicentra, Dolichos, Eranthis, Glycine, Gossypium, Helianthus, Lathyrus, Lens, Lespedeza, Linum, Lotus, Lupinus, Macadamia, Medicago, Melilotus, Mucuna, Olea, Onobrychis, Ornithopus, Oxalis, Papaver, Phaseolus, Phoenix, Pis-*

*tacia, Pisum, Prunus, Pueraria, Ribes, Ricinus, Sesamum, Thalictrum, Theobroma, Trifolium, Trigonella, Vicia* and *Vigna.*

Preferred dicotyledonous species include: *Amygdalus communis, Anacardium occidentale, Anemone americana, Anemone occidentalis, Arachis hypogaea, Arachis hypogea, Brassica napus Rape, Brassica nigra, Brassica campestris, Cajanus cajan, Cajanus indicus, Cannabis sativa, Carthamus tinctorius, Carya illinoinensis, Ceiba pentandra, Cicer arietinum, Claytonia exigua, Claytonia megarhiza, Coriandrum sativum, Coronilla varia, Corydalis flavula, Corydalis sempervirens, Crotalaria juncea, Cyclamen coum, Dentaria laciniata, Dicentra eximia, Dicentra formosa, Dolichos lablab, Eranthis hyemalis, Gossypium arboreum, Gossypium nanking, Gossypium barbadense, Gossypium herbaceum, Gossypium hirsutum, Glycine max, Glycine ussuriensis, Glycine gracilis, Helianthus annus, Lupinus angustifolius, Lupinus luteus, Lupinus mutabilis, Lespedeza sericea, Lespedeza striata, Lotus uliginosus, Lathyrus sativus, Lens culinaris, Lespedeza stipulacea, Linum usitatissimum, Lotus corniculatus, Lupinus albus, Medicago arborea, Medicago falcate, Medicago hispida, Medicago officinalis, Medicago sativa* (alfalfa), *Medicago tribuloides, Macadamia integrifolia, Medicago arabica, Melilotus albus, Mucuna pruriens, Olea europaea, Onobrychis viciifolia, Ornithopus sativus, Oxalis tuberosa, Phaseolus aureus, Prunus cerasifera, Prunus cerasus, Phaseolus coccineus, Prunus domestica, Phaseolus lunatus, Prunus. maheleb, Phaseolus mungo, Prunus. persica, Prunus. pseudocerasus, Phaseolus vulgaris, Papaver somniferum, Phaseolus acutifolius, Phoenix dactylifera, Pistacia vera, Pisum sativum, Prunus amygdalus, Prunus armeniaca, Pueraria thunbergiana, Ribes nigrum, Ribes rubrum, Ribes grossularia, Ricinus communis, Sesamum indicum, Thalictrum dioicum, Thalictrum flavum, Thalictrum thalictroides, Theobroma cacao, Trifolium augustifolium, Trifolium diffusum, Trifolium hybridum, Trifolium incarnatum, Trifolium ingrescens, Trifolium pratense, Trifolium repens, Trifolium resupinatum, Trifolium subterraneum, Trifolium alexandrinum, Trigonella foenumgraecum, Vicia angustifolia, Vicia atropurpurea, Vicia calcarata, Vicia dasycarpa, Vicia ervilia, Vaccinium oxycoccos, Vicia pannonica, Vigna sesquipedalis, Vigna sinensis, Vicia villosa, Vicia faba, Vicia sative* and *Vigna angularis.*

Preferred monocotyledonous genera include: *Agropyron, Allium, Alopecurus, Andropogon, Arrhenatherum, Asparagus, Avena, Bambusa, Bellavalia, Brimeura, Brodiaea, Bulbocodium, Bothrichloa, Bouteloua, Bromus, Calamovilfa, Camassia, Cenchrus, Chionodoxa, Chloris, Colchicum, Crocus, Cymbopogon, Cynodon, Cypripedium, Dactylis, Dichanthium, Digitaria, Elaeis, Eleusine, Eragrostis, Eremurus, Erythronium, Fagopyrum, Festuca, Fritillaria, Galanthus, Helianthus, Hordeum, Hyacinthus, Hyacinthoides, Ipheion, Iris, Leucojum, Liatris, Lolium, Lycoris, Miscanthis, Miscanthus x giganteus, Muscari, Ornithogalum, Oryza, Panicum, Paspalum, Pennisetum, Phalaris, Phleum, Poa, Puschkinia, Saccharum, Secale, Setaria, Sorghastrum, Sorghum, Triticum, Vanilla, X Triticosecale Triticale* and *Zea.*

Preferred monocotyledonous species include: *Agropyron cristatum, Agropyron desertorum, Agropyron elongatum, Agropyron intermedium, Agropyron smithii, Agropyron spicatum, Agropyron trachycaulum, Agropyron trichophorum, Allium ascalonicum, Allium cepa, Allium chinense, Allium porrum, Allium schoenoprasum, Allium fistulosum, Allium sativum, Alopecurus pratensis, Andropogon gerardi, Andropogon Gerardii, Andropogon scoparious, Arrhenatherum elatius, Asparagus officinalis, Avena nuda, Avena sativa, Bambusa vulgaris, Bellevalia trifoliate, Brimeura amethystina, Brodiaea californica, Brodiaea coronaria, Brodiaea elegans, Bulbocodium versicolor, Bothrichloa barbinodis, Bothrichloa ischaemum, Bothrichloa saccharoides, Bouteloua curipendula, Bouteloua eriopoda, Bouteloua gracilis, Bromus erectus, Bromus inermis, Bromus riparius, Calamovilfa longifilia, Camassia scilloides, Cenchrus ciliaris, Chionodoxa forbesii, Chloris gayana, Colchicum autumnale, Crocus sativus, Cymbopogon nardus, Cynodon dactylon, Cypripedium acaule, Dactylis glomerata, Dichanthium annulatum, Dichanthium aristatum, Dichanthium sericeum, Digitaria decumbens, Digitaria smutsii, Elaeis guineensis, Elaeis oleifera, Eleusine coracan, Elymus angustus, Elymus junceus, Eragrostis curvula, Eragrostis tef Eremurus robustus, Erythronium elegans, Erythronium helenae, Fagopyrum esculentum, Fagopyrum tataricum, Festuca arundinacea, Festuca ovina, Festuca pratensis, Festuca rubra, Fritillaria cirrhosa, Galanthus nivalis, Helianthus annuus sunflower, Hordeum distichum, Hordeum vulgare, Hyacinthus orientalis, Hyacinthoides hispanica, Hyacinthoides non-scripta, Ipheion sessile, Iris collettii, Iris danfordiae, Iris reticulate, Leucojum aestivum, Liatris cylindracea, Liatris elegans, Lilium longiflorum, Lolium multiflorum, Lolium perenne, Lycoris radiata, Miscanthis sinensis, Miscanthus x giganteus, Muscari armeniacum, Muscari macrocarpum, Narcissus pseudonarcissus, Ornithogalum montanum, Oryza sativa, Panicum italicium, Panicum maximum, Panicum miliaceum, Panicum purpurascens, Panicum virgatum, Paspalum dilatatum, Paspalum notatum, Pennisetum clandestinum, Pennisetum glaucum, Pennisetum purpureum, Pennisetum spicatum, Phalaris arundinacea, Phleum bertolinii, Phleum pratense, Poa fendleriana, Poa pratensis, Poa nemoralis, Puschkinia scilloides, Saccharum officinarum, Saccharum robustum, Saccharum sinense, Saccharum spontaneum, Scilla autumnalis, Scilla peruviana, Secale cereale, Setaria italica, Setaria sphacelata, Sorghastrum nutans, Sorghum bicolor, Sorghum dochna, Sorghum halepense, Sorghum sudanense, Trillium grandiflorum, Triticum aestivum, Triticum dicoccum, Triticum durum, Triticum monococcum, Tulipa batalinii, Tulipa clusiana, Tulipa dasystemon, Tulipa gesneriana, Tulipa greigii, Tulipa kaufmanniana, Tulipa sylvestris, Tulipa turkestanica, Vanilla fragrans, X Triticosecale* and *Zea mays.*

Other preferred plants are forage plant species from a group comprising but not limited to the following genera: *Lolium, Festuca, Dactylis, Bromus, Trifolium, Medicago, Pheleum, Phalaris, Holcus, Lotus, Plantago* and *Cichorium.*

Particularly preferred genera are *Lolium* or *Trifolium*. Particularly preferred are the species *Lolium Perenne* and *Trifolium repens*. Most preferred is the species *Lolium perenne*.

The term "plant" is intended to include a whole plant, any part of a plant, fruit, seed, harvested material, propagules and progeny of a plant.

The term 'propagule' means any part of a plant that may be used in reproduction or propagation, either sexual or asexual, including seeds and cuttings.

The plants of the invention may be grown and either selfed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the invention.

Preferably the plant, plant part, fruit, seed, harvested material, plant propagule or plant progeny contains the polynucleotide that was transformed into the parent plant. Preferably the plant, plant part, fruit, seed, harvested material, plant propagule or plant progeny expresses the polynucleotide that was transformed into the parent plant.

DETAILED DESCRIPTION

Definitions

The term "comprising" as used in this specification and claims means "consisting at least in part of"; that is to say when interpreting statements in this specification and claims which include "comprising", the features prefaced by this term in each statement all need to be present but other features can also be present. Related terms such as "comprise" and "comprised" are to be interpreted in similar manner.

The term "tolerance or tolerant to drought stress" is intended to describe a plant or plants which perform more favourably in any aspect of their growth and development under, or after, sub-optimal hydration conditions than do suitable control plants in the same conditions.

The term "tolerance or tolerant to cold stress" is intended to describe a plant or plants which perform more favourably in any aspect of their growth and development under, or after, sub-optimal-reduced temperature conditions than do suitable control plants in the same conditions.

The term "tolerance or tolerant to freezing stress" is intended to describe a plant or plants that perform more favourably in any aspect of their growth and development under, or after, temperature conditions of less than or equal to 0° C., than do suitable control plants in the same conditions.

The term "tolerance or tolerant to heat stress" is intended to describe a plant or plants that perform more favourably in any aspect of their growth and development under, or after, sub-optimal elevated temperature conditions than do suitable control plants in the same conditions.

The term "tolerance or tolerant to salinity" is intended to describe a plant or plants that perform more favourably in any aspect of their growth and development under, or after, sub-optimal elevated salinity conditions than do suitable control plants in the same conditions.

Suitable control plants may include non-transformed plants of the same species or variety, or plants of the same species or variety transformed with a control construct.

With reference to the selection methods of the invention, a plant with increased tolerance to environmental stress refers to a plant, selected from a population of plants, which performs more favourably in any aspect of growth and development under stress conditions than does an average member of the population under the same conditions.

The more favourable performance referenced to above includes improved performance after the environmental stress is removed, that is improved recovery after a period of environmental stress.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides that is capable of specific hybridization to a target of interest, e.g., a sequence that is at least 15 nucleotides in length. The fragments of the invention comprise 15 nucleotides, preferably at least 20 nucleotides, more preferably at least 30 nucleotides, more preferably at least 50 nucleotides, more preferably at least 50 nucleotides, more preferably at least 60 nucleotides, more preferably at least 70 nucleotides, more preferably at least 80 nucleotides, more preferably at least 90 nucleotides, more preferably at least 100 nucleotides, more preferably at least 150 nucleotides, more preferably at least 200 nucleotides, more preferably at least 250 nucleotides, more preferably at least 300 nucleotides, more preferably at least 350 nucleotides, more preferably at least 400 nucleotides, more preferably at least 450 nucleotides of contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods of the invention.

The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence, that is complementary to the probe, in a hybridization-based assay. The probe may consist of a "fragment" of a polynucleotide as defined herein.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed or purified from their natural cellular environment. An isolated molecule may be obtained by any method or combination of methods including biochemical, recombinant, and synthetic techniques. A isolated polynucleotide of the invention may be inserted/transformed into a plant, including a plant of the same species from which it was originally isolated. The invention is intended to encompass such plants and their off-spring, that comprise the transformed polynucleotide, even though the polynucleotide could be described as having been returned to its natural environment.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genera or species, means that the polynucleotide or polypeptide has the same sequence as a polynucleotide or polypeptide found naturally in that genera or species. The polynucleotide or polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polypeptides possess biological activities that are the same or similar to those of the inventive polypeptides or polypeptides. The term "variant" with reference to polypeptides and polypeptides encompasses all forms of polypeptides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a specified polynucleotide sequence. Identity is found over a comparison window of at least 20 nucleotide positions, preferably at least 40 nucleotide positions, preferably at least 60 nucleotide positions, preferably at least 80 nucleotide positions, more preferably at least 100 nucleotide positions, and most preferably over the entire length of the specified polynucleotide sequence.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI (ftp<dot>ncbi<dot>nih<dot>gov/blast). The default parameters of bl2seq are utilized except that filtering of low complexity parts should be turned off.

The identity of polynucleotide sequences may be examined using the following unix command line parameters:
bl2seq -i nucleotideseq1 -j nucleotideseq2 -F F -p blastn The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Bioi. 48, 443-453). A full implementation of the Needleman-Wunsch global alignment algorithm is found in the needle program in the EMBOSS package (Rice,P. Longden,!. and Bleasby,A. EMBOSS: The European Molecular Biology Open Software Suite, Trends in Genetics Jun. 2000, vol 16, No 6. pp.276-277) which can be obtained from www<dot>hgmp<dot>mrc<dot>ac<dot>uk/Software/EMBOSS/. The European Bioinformatics Institute server also provides the facility to perform EMBOSS-needle global alignments between two sequences on line at www<dot>ebi<dot>ac <dot>uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ftp<dot>ncbi<dot>nih<dot>gov/blast/).

The similarity of polynucleotide sequences may be examined using the following unix command line parameters:
bl2seq -i nucleotideseq1 -j nucleotideseq2 -F F -p tblastx The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-10}$ more preferably less than $1\times10^{-20}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$, more preferably less than $1\times10^{-100}$, more preferably less than $1\times10^{-110}$ and most preferably less than $1\times10^{-120}$ when compared with any one of the specifically identified sequences.

Alternatively, variant polynucleotides of the present invention hybridize to a specified polynucleotide sequence, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing,). Tm for polynucleotide molecules greater than about 100 bases can be calculated by the formula Tm=81.5+0.41% (G+C-log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for a polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides of the present invention also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from NCBI (ftp<dot>ncbi<dot>nih<dot>gov/blast/) via the tblastx algorithm as previously described.

The function of a variant polynucleotide of the invention in modulating tolerance to environmental stress plant may be assessed by altering expression of the polynucleotide in a plant by methods known in the art and/or described herein, and, analyzing performance of the transformed plant in comparison to a control plant, under conditions of environmental stress. Further plant transformation protocols for several species are known to those skilled in the art. A list of such protocols is provided herein.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 40 amino acid positions, more preferably at least 60 amino acid positions, and most preferably over the whole length of the sequence of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from NCBI (ftp<dot>ncbi<dot>nih<dot>gov/blast/). The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at http:/www.ebi.ac.uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

Use of BLASTP as described above is preferred for use in the determination of polypeptide variants according to the present invention.

Polypeptide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ftp<dot>ncbi<dot>nih<dot>gov/blast/). The similarity of polypeptide sequences may be examined using the following unix command line parameters:

bl2seq -i peptideseq1 -j peptideseq2 -F F -p blast

Variant polypeptide sequences preferably exhibit an E value of less than $1\times10^{-10}$ more preferably less than $1\times10^{-20}$, more preferably less than $1\times10^{-30}$, more preferably less than $1\times10^{-40}$, more preferably less than $1\times10^{-50}$, more preferably less than $1\times10^{-60}$ more preferably less than $1\times10^{-70}$, more preferably less than $1\times10^{-80}$, more preferably less than $1\times10^{-90}$, more preferably less than $1\times10^{-100}$ more preferably less than $1\times10^{-110}$, more preferably less than $1\times10^{-120}$ and most preferably less than $1\times10^{-123}$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as *E. coli*.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:
 a) a promoter functional in the host cell into which the construct will be transformed,
 b) the polynucleotide to be expressed, and
 c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors.

A "transgene" is a polynucleotide that is taken from one organism and introduced into a different organism by transformation. The transgene may be derived from the same species or from a different species as the species of the organism into which the transgene is introduced.

An "inverted repeat" is a sequence that is repeated, where the second half of the repeat is in the complementary strand, e.g.,

```
(5')GATCTA . . . TAGATC(3')
(SEQ ID NO: 32)

(3')CTAGAT . . . ATCTAG(5')
(SEQ ID NO: 32)
```

Read-through transcription will produce a transcript that undergoes complementary base-pairing to form a hairpin structure provided that there is a 3-5 bp spacer between the repeated regions.

A "transgenic plant" refers to a plant which contains new genetic material as a result of genetic manipulation or transformation. The new genetic material may be derived from a plant of the same species as the resulting transgenic plant or from a different species.

The terms "to alter expression of" and "altered expression" of a polynucleotide or polypeptide of the invention, are intended to encompass the situation where genomic DNA corresponding to a polynucleotide of the invention is modified thus leading to altered expression of a polynucleotide or polypeptide of the invention. Modification of the genomic DNA may be through genetic transformation or other methods known in the art for inducing mutations. The "altered expression" can be related to an increase or decrease in the amount of messenger RNA and/or polypeptide produced and may also result in altered activity of a polypeptide due to alterations in the sequence of a polynucleotide and polypeptide produced.

The applicants have identified a polynucleotide from ryegrass (SEQ ID NO:1) which encode a polypeptide (SEQ ID NO:10) which modulates in plants, tolerance to at least one environmental stress selected from drought, cold, freezing, heat and salinity. The applicants have also identified polynucleotide variants of SEQ ID NO:1 (SEQ ID NO:2 to 9) encoding polypeptide variants of SEQ ID NO:10 (SEQ ID NO:11 to 18) which modulate in plants, tolerance to at least one environmental stress selected from drought, cold, freezing, heat and salinity.

The invention provides plants altered, relative to suitable control plants, in tolerance to at least one environmental stress selected from drought, cold, freezing, heat and salinity. The invention provides both plants with both increased tolerance to the above and plants with decreased tolerance to the above stresses. The invention also provides methods for the production or selection of such plants.

Methods for Isolating or Producing Polynucleotides

The polynucleotide molecules of the invention can be isolated by using a variety of techniques known to those of ordinary skill in the art. By way of example, such polynucleotides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides, of the invention or useful in the methods of the invention, include use of all, or portions of, the polynucleotides set forth herein as hybridization probes. The technique of hybridizing labeled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0.5% sodium dodecyl sulfate, 1× Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion and oligonucleotide synthesis.

A partial polynucleotide sequence may be used, in methods well-known in the art to identify the corresponding full length polynucleotide sequence. Such methods include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, *Nucleic Acids Res* 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species. Variants (including orthologues) may be identified by the methods described.

Methods for Identifying Variants

Physical Methods

Variant polynucleotides may be identified using PCR-based methods (Mullis et al., Eds. 1994 The Polymerase Chain Reaction, Birkhauser). Typically, the polynucleotide sequence of a primer, useful to amplify variant polynucleotide molecules PCR, may be based on a sequence encoding a conserved region of the corresponding amino acid sequence.

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

Polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp<dot>ncbi<dot>nih<dot>gov/blast/) or from the National Center for Biotechnology Information (NCB I), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J.D., Higgins, D.G. and Gibson, T.J. (1994) CLUSTALW: improving the sensitivity of progressive multiple sequence alignment through sequence weighting, positions-specific gap penalties and weight matrix choice. Nucleic Acids Research, 22:4673-4680, www-igbmc<dot>u-strasbg<dot>fr/BioInfo/ClustalW/Top<dot>html) or T-COFFEE (Cedric Notredame, Desmond G. Higgins, Jaap Heringa, T-Coffee: A novel method for fast and accurate multiple sequence alignment, J. Mol. Bioi. (2000) 302: 205-217))or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Isolating Polypeptides

The polypeptides of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco, Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention may also be purified from natural sources using a variety of techniques that are well known in the art (e.g. Deutscher, 1990, Ed, Methods in Enzymology, Vol. 182, *Guide to Protein Purification,*).

Alternatively the polypeptides and variant polypeptides of the invention may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Constructs and Vectors

The invention provides a host cell which comprises a genetic construct or vector of the invention. Host cells may be derived from, for example, bacterial, fungal, insect, mammalian or plant organisms.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Host cells of the invention may also be useful in methods for production of an enzymatic product generated by an expressed polypeptide of the invention. Such methods may involve culturing the host cells of the invention in a medium suitable for expression of a recombinant polypeptide of the invention, optionally in the presence of additional enzymatic substrate for the expressed polypeptide of the invention. The enzymatic product produced may then be separated from the host cells or medium by a variety of art standard methods.

Methods for Producing Plant Cells and Plants Comprising Constructs and Vectors

The invention further provides plant cells which comprise a genetic construct of the invention, and plant cells modified to alter expression of a polynucleotide or polypeptide of the invention. Plants comprising such cells also form an aspect of the invention.

Production of plants altered in tolerance to environmental stress may be achieved through methods of the invention. Such methods may involve the transformation of plant cells and plants, with a construct designed to alter expression of a polynucleotide or polypeptide capable of modulating tolerance to environmental stress in such plant cells and plants. Such methods also include the transformation of plant cells and plants with a combination of constructs designed to alter expression of one or more polypeptides or polypeptides capable of modulating tolerance to environmental stress in such plant cells and plants.

Methods for transforming plant cells, plants and portions thereof with polynucleotides are described in Draper et al., 1988, Plant Genetic Transformation and Gene Expression. A Laboratory Manual. Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of strategies for genetically manipulating plants are available (e.g. Birch, 1997, Ann Rev Plant Phys Plant Mol Biol, 48, 297). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detest presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zin gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenbert. Eds) Springer Verlag. Berline, pp. 325-336.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide of the invention may include an antisense copy of a polynucleotide of the invention. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

```
5'GATCTA 3'          3'CTAGAT 5' (antisense strand)
(coding strand)

3'CUAGAU 5' mRNA    5'GAUCUCG 3' antisense RNA
```

Genetic constructs designed for gene silencing may also include an inverted repeat. An 'inverted repeat' is a sequence that is repeated where the second half of the repeat is in the complementary strand, e.g.,

```
        5'-GATCTA . . . TAGATC-3'
        (SEQ ID NO: 32)

3'-CTAGAT . . . ATCTAG-5'
        (SEQ ID NO: 32)
```

The transcript formed may undergo complementary base pairing to form a hairpin structure. Usually a spacer of at least 3-5 bp between the repeated region is required to allow hairpin formation.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polynucleotides useful for effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve overexpression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a polynucleotide of the invention is also contemplated.

The polynucleotide inserts in genetic constructs designed for gene silencing may correspond to coding sequence and/or non-coding sequence, such as promoter and/or intron and/or 5' or 3' UTR sequence, or the corresponding gene.

Other gene silencing strategies include dominant negative approaches and the use of ribozyme constructs (McIntyre, 1996, Transgenic Res, 5, 257)

Pre-transcriptional silencing may be brought about through mutation of the gene itself or its regulatory elements. Such mutations may include point mutations, frameshifts, insertions, deletions and substitutions.

The following are representative publications disclosing genetic transformation protocols that can be used to genetically transform the following plant species: Rice (Alam et al., 1999, Plant Cell Rep. 18, 572); maize (U.S. Pat. Ser. Nos. 5,177,010 and 5,981,840); wheat (Ortiz et al., 1996, Plant Cell Rep. 15, 1996, 877); tomato (U.S. Pat. Ser. No. 5,159, 135); potato (Kumar et al., 1996 Plant J. 9: 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Ser. Nos. 5,846, 797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. Ser. No. 5,792,935); soybean (U.S. Pat. Nos. 5,416, 011; 5,569,834; 5,824,877; 5,563,04455 and 5,968,830); pineapple (U.S. Pat. Ser. No. 5,952,543); poplar (U.S. Pat. No. 4,795,855); monocots in general (U.S. Pat. Nos. 5,591, 616 and 6,037,522); *brassica* (U.S. Pat. Nos. 5,188,958; 5,463,174 and 5,750,871); and cereals (U.S. Pat. No. 6,074, 877). Other species are contemplated and suitable methods and protocols are available to in the scientific literature for use by those skilled in the art.

Several further methods known in the art may be employed to alter expression of a nucleotide and/or polypeptide of the invention. Such methods include but are not limited to Tilling (Till et al., 2003, Methods Mol Biol, 2%, 205), so called "Deletagene" technology (Li et al., 2001, Plant Journal 27(3), 235) and the use of artificial transcription factors such as synthetic zinc finger transcription factors. (e.g. Jouvenot et al., 2003, Gene Therapy 10, 513). Additionally antibodies or fragments thereof, targeted to a particular polypeptide may also be expressed in plants to modulate the activity of that polypeptide (Jobling et al., 2003, Nat. Biotechnol., 21(1), 35). Transposon tagging approaches may also be applied. Additionally peptides interacting with a polypeptide of the invention may be identified through technologies such as phase-display (Dyax Corporation). Such interacting peptides may be expressed in or applied to a plant to affect activity of a polypeptide of the invention. Use of each of the above approaches in alteration of expression of a nucleotide and/or polypeptide of the invention is specifically contemplated.

Methods for Selecting Plants

Methods are also provided for selecting plants with altered tolerance to environmental stress. Such methods involve testing of plants for altered for the expression of a polynucleotide or polypeptide of the invention. Such methods may be applied at a young age or early developmental stage when the altered tolerance to environmental stress may not necessarily be visible, to accelerate breeding programs directed toward improving tolerance to environmental stress.

The expression of a polynucleotide, such as a messenger RNA, is often used as an indicator of expression of a corresponding polypeptide. Exemplary methods for measuring the expression of a polynucleotide include but are not limited to Northern analysis, RT-PCR and dot-blot analysis (Sambrook et al., Molecular Cloning: A Laboratory Manual, 2nd Ed. Cold Spring Harbor Press, 1987). Polynucleotides or portions of the polynucleotides of the invention are thus useful as probes or primers, as herein defined, in methods for the identification of plants with altered tolerance to environmental stress. The polypeptides of the invention may be used as probes in hybridization experiments, or as primers in PCR based experiments, designed to identify such plants.

Alternatively antibodies may be raised against polypeptides of the invention. Methods for raising and using antibodies are standard in the art (see for example: Antibodies, A Laboratory Manual, Harlow A Lane, Eds, Cold Spring Harbour Laboratory, 1998). Such antibodies may be used in methods to detect altered expression of polypeptides which modulate tolerance to environmental stress in plants. Such methods may include ELISA (Kemeny, 1991, A Practical Guide to ELISA, NY Pergamon Press) and Western analysis (Towbin & Gordon, 1994, J Immunol Methods, 72, 313).

These approaches for analysis of polynucleotide or polypeptide expression and the selection of plants with altered expression are useful in conventional breeding programs designed to produce varieties with altered tolerance to environmental stress.

Plants

The plants of the invention may be grown and either self-ed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the present invention.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

The present invention will be better understood with reference to the accompanying drawings in which:

FIG. 2 shows the sequence (SEQ ID NO:23) of the pCORF135 vector, corresponding to the map in FIG. 1. Sequence in bold corresponds to the Double CaMV35S promoter. Sequence in italics corresponds to ORF135. Sequence underlined corresponds to 3'terminator sequence from CaMV35S gene. Sequence in regular font corresponds to vector sequence and other genetic elements in the vector.

FIG. 3 shows a Clustal W (1.83) multiple sequence alignment of the ORF135 polypeptide of SEQ ID NO:10 and sequences, which are variants of SEQ ID NO:10, from several species and illustrates conserved amino acids shown by asterisks. The alignment is repeated in each of panels A-D. Panel A highlights a consensus motif completely conserved in all viridiplantae sequences. Panel B highlights a consensus motif completely conserved in all plant sequences. Panel C highlights a consensus motif completely conserved in all motocotyledonous plant sequences. Panel D highlights a consensus motif completely conserved in all dicotyledonous sequences.

FIG. 11 shows the cDNA sequence of ORF135. Bold ATG shows the position of the start codon. Bold TGA shows the position of the stop codon. Underlined ACTGTTGACA(SEQIDNO:33) shows the position of the SAGE tag. The coding sequence is the sequence from the bold ATG to the bold TGA.

EXAMPLES

Figure 1:
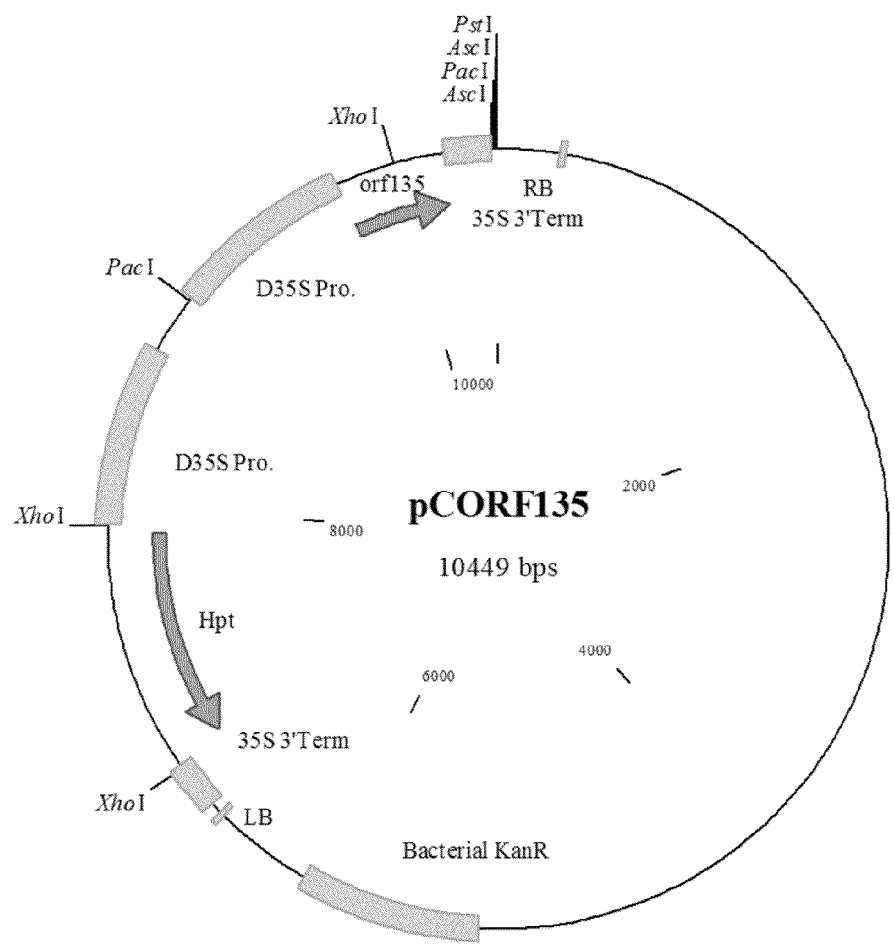
FIG. 1 shows a map of a vector (pCORF135), for plant transformation, comprising ORF135 (SEQ ID NO:1) operably linked to the constitutive Double CaMV35S promoter.
Figure 4:
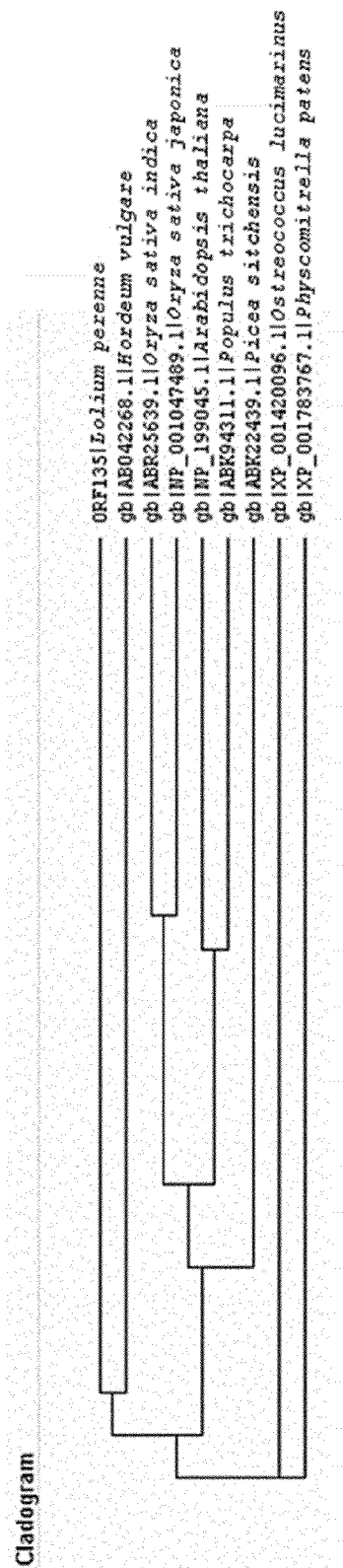
FIG. 4 shows a cladogram of the protein sequences in FIG. 3.
Figure 5:
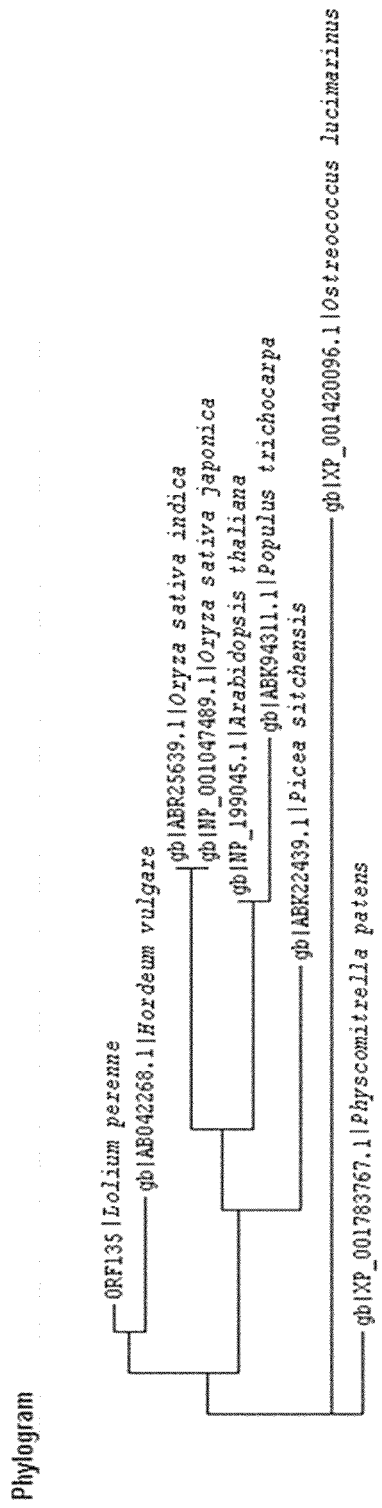
FIG. 5 shows a phylogram of the protein sequences in FIG. 3.

The invention will now be illustrated with reference to the following non-limiting examples.

Example 1

Identification of Polynucleotides which Modulate Tolerance to Environmental Stresses Introduction:

Perennial ryegrass (*Lolium perenne* L.) is a cool temperate pasture plant from the family Gramineae and the tribe Festucaceae. To generate a profile of relative gene expression patterns in ryegrass, RNA was extracted from samples obtained from ambient temperature growth, cold grown, hydrated, dehydrated and rehydrated or dehydration pre- and post-grazed plants during autumn, summer, spring and winter, and used for constructing a SAGE (serial analysis of gene expression) (Velculescu et al. 1995, *Science* 270: 484-487) library.

Materials and Methods:

Perennial ryegrass (*Lolium perenne* L.) cv. Bronsyn was used throughout this study. Field grown samples were collected from active paddocks at Dexcel, Hamilton, New Zealand during the peak of each season. Grass samples were collected from pre-grazed (15 days post grazing) and post-grazed (1 day post grazing) ryegrass swards. Tufts of grass samples were harvested from 3-6 randomly chosen sites and stored in dry-ice after snap-freezing with liquid nitrogen. During spring, immature spike and floral initials were also harvested. For stress-treatment, the following conditions were used on lab-grown ryegrass: Mature lab-grown perennial ryegrass that was grown in growth chamber for 15 months at 85% RH, 20° C./18° C. and 16 h/8 h day/night regime; Hydrated control grown for 55 days at 85% RH, 20° C./18° C. and 16 h/8 h day/night regime; 6 days at 70% RH, 22° C./16° C. and 16 h/8 h day/night regime, seedlings were kept watered throughout their life; Dehydrated sample watered only for 55 days at 85% RH, 20° C./18° C. and 16 h/8 h day/night regime; 3 days at 70% RH, 28° C./20° C. and 16 h/8 h day/night regime; 3 days at 50% RH, 28° C./20° C. and 16 h/8 h day/night regime; Rehydrated samples were from dehydrated plants that was watered for 24 hours and grown at 70% RH, 22° C./16° C. and 16 h/8 h day/night regime; Cold-stressed plants were grown for 55 days at 85% RH, 20° C./18° C. and 16 h/8 h day/night regime; 7 days at 70% RH, 22° C./16° C. and 16 h/8 h day/night regime; 7 days at 70% RH, 6° C./2° C. and 16 h/8 h day/night regime, seedlings were kept watered throughout their life.

Construction of SAGE Libraries

RNA was extracted using TRIZOL® reagent (Invitrogen, Calif., USA) and by the protocol described by the manufacturer from tissue that was ground in liquid nitrogen. For each SAGE library 100 μg of total RNA was used and the libraries were created using I-SAGE™ or I-SAGE™ Long kit (Invitrogen, Calif., USA) according to manufacturer's protocol. From each library 960-1,920 clones were sequenced (Australian Genome Research Facility, Brisbane, Australia) and the tags extracted using the SAGE2000 software.

SAGE Bioinformatics:

The relational database was designed to hold tags, libraries and expression counts of the SAGE experiments. Each tag sequence (including enzyme sequence) was searched against the whole Ryegrass non-overlapping Gene thresher and the EST sets. The search was carried out in both direction and used exact match only. Results were loaded to the relational database using General Feature Format (GFF) approach www3<dot>ebi<dot>ac<dot>uk/Services/WebFeat).

All Ryegrass Gene thresher and the EST sequences were annotated using homology searches against some or all the following public and propriety databases:

AGI TIGR Gene Indices, *Arabidopsis,* release 11, January 2004

OGI TIGR Gene Indices, Rice, release 14-1, January 2004

GENESEQN Derwent patent DNA sequences 2002 Dec. 7

GENESEQP Derwent patent amino acid sequences 2002 Dec. 7

Os_unigene Oryza sativa Unigene unique sequences 2004 Mar. 18 est_others Other EST sequences (mammal, fungi, prokaryote) 2003 Mar. 11 est_plant Viridiplantae subset of Non-redundant Database of GenBank+EMBL+DDBJ EST Divisions 2004 Mar. 15 nr All non-redundant GenBank CDS translations+PDB+SwissProt+PIR 2003 Mar. 11 nr_plant Plant subset of HS subset of BT subset of All non-redundant GenBank CDS translations+PDB+SwissProt+PIR 2003 Aug. 8 nt All Non-redundant GenBank+EMBL+DDBJ+PDB sequences (but no EST, STS, GSS, or I-ITGS sequences) 2003 Mar. 11 nt_monocots Monocot subset of All Non-redundant GenBank+EMBL+DDBJ+PDB sequences (but no EST, STS, GSS, or HTGS sequences) 2003 Mar. 11 swissprot The last major release of the SWISS-PROT protein sequence database (no updates) 2003 Mar. 28

A cutoff of E value less than E-05 was used and maximum of 10 targets per database were stored in the relational database.

Tags Annotation:

Tags with hits to the Ryegrass sets were annotated by creating a summary of all the annotations of the involved sequences. The summary was generated using an algorithm to calculate the frequency of the occurrence of each word in the annotations and rank them in descending order based on the number off occurrences. The summary was limited to 10 words and a void word list was used to filter out insignificant information. The resulting summary line was used as an indication of what the tags were likely to be. Actual numbers are displayed; giving additional information that could be used to evaluate the significance of each of the words in the summary. This method of automatic annotation using keyword counts is similar to the Automatic comment that is used by the ProDom database (available on the world wide web at http: protein<dot>Toulouse <dot>inra<dot>fr/prodom/currentlhtmllhome<dot>ph) to annotate the automatically generated protein domain families.

Detailed annotation based on the top hits of the involved sequences was displayed when viewing tags data.

A polynucleotide sequence of particular interest was identified by carrying out a BLASTX analysis of the polynucleotide sequences, which had higher frequency of SAGE tags in the dehydrated perennial ryegrass SAGE library, against the peptides encoded by sORFs described in Saccharomyces cerevisiae (Kastenmayer et al. 2006, Genome Res. 16(3): 365-373). The analysis resulted in the identification of ORF135 (corresponds to SEQ ID NO:1).

ORF135 appears to encode a protein similar to HUB1, a type I ubiquitin-like protein modifier (similar to UBL5 from mammals). A distinct enzymatic system exists for each ubiquitin-like protein modifier. The functional consequences of protein modification by ubiquitin-like proteins appear to be distinct from that of ubiquitination, in that ubiquitin-like modifiers do not typically signal the degradation of their protein targets. Ubiquitin-like modifiers may serve instead as reversible modulators of protein function (Dittmar et al. 2002. Science 295 (5564), 2442-2446). Although functionally diverse, ubiquitin-like protein modifiers have a universal sequence feature: a glycine residue at the COOH-terminal site of conjugate formation. However, unlike ubiquitin and all other ubiquitin-like modifiers, HUB1 and its mammalian orthologs UBL5 contain a C-terminal di-tyrosine motif followed by a single variable residue instead of the characteristic di-glycine found in all other ubiquitin-like modifiers (Mc-Nally et al. 2003, Protein Science 12,1562-1566). Although Hub 1 is found to be extremely well conserved in evolution, more so than any other ubiquitin-like protein, no specific segment of Hub 1 is significantly related to ubiquitin or to any ubiquitin-like protein (Dittmar et al. 2002. Science 295 (5564), 2442-2446). Hence, Hub1 is said to be the most divergent of ubiquitin-like modifiers, or alternatively its similarity to ubiquitin may simply reflect a shared folding topology (Dittmar et al. 2002. Science 295 (5564), 2442-2446). Although the ORF135 transcript is present in all perennial ryegrass SAGE libraries created, it has an enhanced expression in dehydrated, mature and summer-grown tissues. The full transcript profile is shown in table 1.

TABLE 1

| SAGE_TAG | ACTGTTGACA (SEQ ID NO 33) | tpm* | SAGE_TAG | ACTGTTGACAGCTTGAA (SEQ ID NO 34) | tpm |
| --- | --- | --- | --- | --- | --- |
| Winter Pre-grazed | 3 | 129 | Winter Pre-grazed | 3 | 108 |
| Winter Post-grazed | 3 | 128 | Winter Post-grazed | 3 | 112 |
| Winter roots | 1 | 76 | Winter roots | 1 | 61 |
| Spring Pre-grazed | 1 | 60 | Spring Pre-grazed | 1 | 53 |
| Spring Post-grazed | 3 | 208 | Spring Post-grazed | 3 | 182 |
| Inflorescence | 2 | 102 | Inflorescence | 2 | 82 |
| Summer Post-grazed | 7 | 413 | Summer Post-grazed | 7 | 360 |
| Autumn Pre-grazed | 5 | 193 | | | |
| Autumn Post-grazed | 4 | 163 | | | |
| Mature | 9 | 847 | | | |
| Cold-stressed | 4 | 249 | | | |
| Hydrated | 3 | 224 | | | |
| Dehydrated | 5 | 361 | | | |
| Rehydrated | 3 | 114 | | | |

*tpm = Tag counts per million tags

Example 2

Identification Variants of ORF135

The ORF135 polynucleotide sequence was used as seed sequence to perform a discontiguous megablast BLASTN search against i) GenBank nucleotide collection NR/NT database (v2.2.18 release date Mar. 2, 2008) and ii) patent sequences database (v2.2.18 release date Mar. 2, 2008).

The polypeptide sequence encoded by the ORF135 was used as seed sequence to perform Position-Specific Iterated BLASTP search against GenBank NR database (v2.2.18 release date Mar. 2, 2008). Besides a PSI-BLASTP, a NCBI-BLASTP search was also performed against UniRef100 protein database at EBI (v2.2.17 release date Aug. 26, 2007).

The applicants identified variants of ORF135 from several species. The polynucleotide variants of SEQ ID NO: 2 to 9 encode the polypeptide variants of SEQ ID NO: 11 to 18 respectively.

Figure 3:
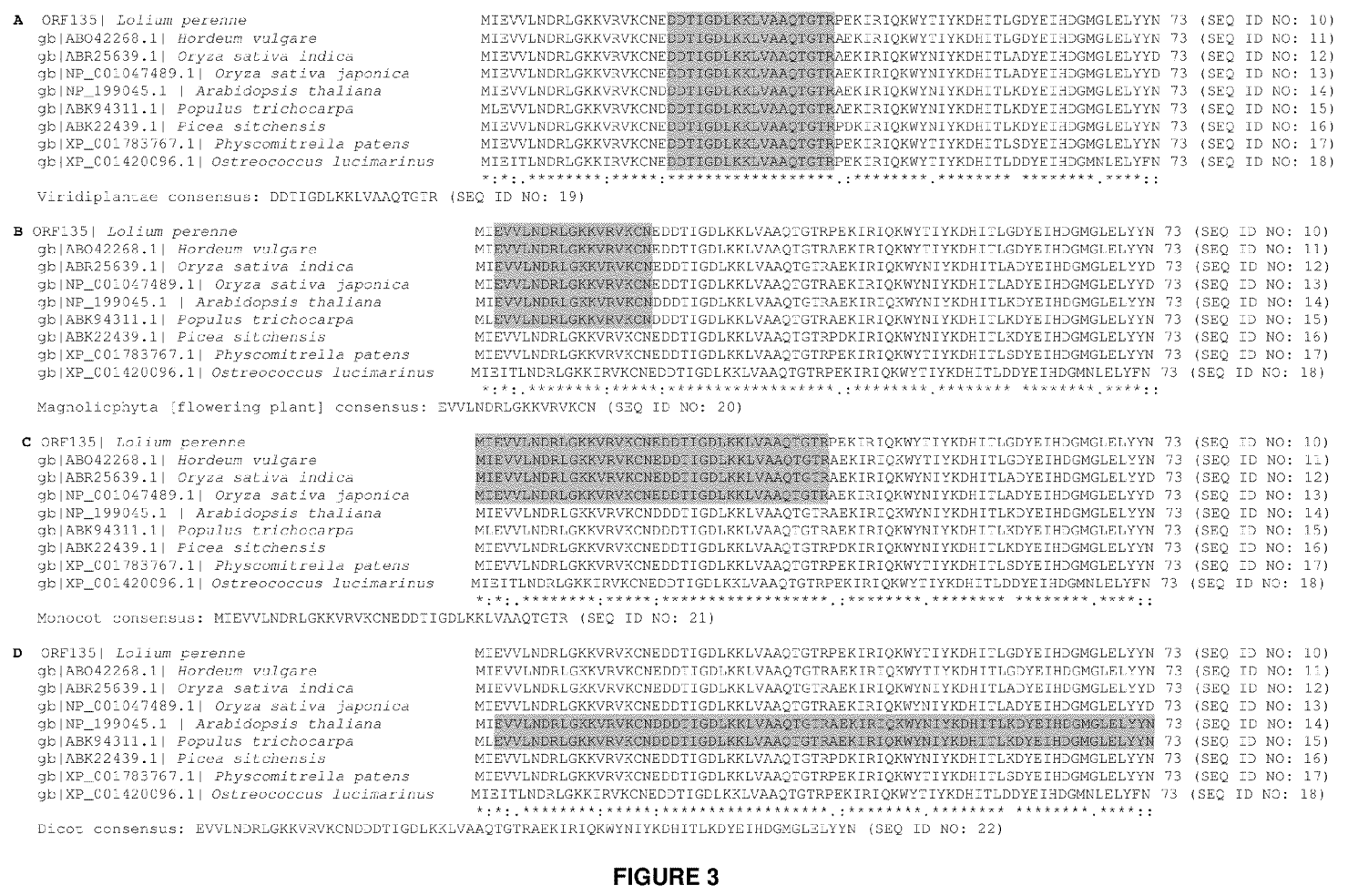

The variant polypeptide sequences, all of which are from Viridiplantae, were aligned using the popular multiple alignment program ClustalW (FIG. 3). Although the selected polypeptide sequences used ranged from the simplest unicellular plankton to evolutionarily advanced monocots, the peptide sequences varied in only twelve residues. Moreover, at the variable positions the residues were usually swapped for another similar residue.

The applicants also identified motifs that are completely conserved in: all of the viridiplantae sequences (SEQ ID NO:19), all of the plant sequences (SEQ ID NO:20), all of the monocotyledonous plant sequences (SEQ ID NO:21), and all of the dicotyledonous plant sequences (SEQ ID NO:22). Theses conserved motifs are highlighted in FIG. 3 in panels A, B, C and D respectively.

Example 3

Transformation of Plants with the Polynucleotides of the Invention

Vector Preparation

A vector for over-expressing ORF135 was produced by standard molecular biology techniques. A map of the vector (pCORF135) is shown in FIG. 1. The sequence of the vector is shown in FIG. 2 and SEQ ID NO:23.

Plant Transformation

Perennial ryegrass (*Lolium perenne* L. cv. Impact) was transformed essentially as described in Bajaj et. al. (Plant Cell Reports, 2006, 25: 651-659). Embryogenic callus derived from mersitematic regions of the tillers of selected ryegrass lines and *Agrobacterium tumefaciens* strain EHA101 carrying a modified binary vector (FIG. 1) was used for transformation experiments. Embryogenic calli were immersed with overnight-grown *Agrobacterium* cultures for 30 minutes with continuous shaking. Calli resistant to hygromycin were selected after subculturing them on co-cultivation medium for 4 weeks. After selection, the resistant calli were subcultured on regeneration medium every 2 weeks until the plants regenerated. The regenerants that continued to grow after two or three rounds of selection proved to be stable transformants. Each regenerated plant was then multiplied on maintenance medium to produce clonal plantlets and subsequently rooted on MS medium without hormones. A rooted plant from each clone was transferred into contained glasshouse conditions while retaining a clonal counterpart in tissue culture as backup. We analyzed plants obtained from one non-transgenic control and three independent transgenic events (ORF135-1, ORF135-2 and ORF135-3) in a climate-controlled environmental laboratory (FIG. 6), where they are subjected to three cycles of drought-stress (FIG. 7), which increased in duration successively as discussed in Example 4.

Southern Blot Analysis of Transformants

Genomic DNA was isolated from transformed and non-transformed control lines of *Lolium perenne*. Approximately 1.5 g of leaf blade and pseudostem material was harvested from each line. Tissue was ground to a powder in a mortar and pestle with liquid Nitrogen and stored in a 50 mL tube at −80° C. until extraction. DNA was isolated from the prepared tissue essentially as described in Doyle and Doyle, 1990 (Doyle J. J. and Doyle J. L. 1990. Isolation of plant DNA from fresh tissue. Focus 12:13-15). Extracted DNA was resuspended in 800 µl TE and the concentration was estimated using a Nanodrop N1000.

Approximately 25 µg genomic DNA's were digested with restriction enzymes EcoRV and SpeI. DNA was digested overnight at 37° C. with 40 units of restriction enzyme in a 100 µl reaction volume. A further 20 units of enzyme was added after 12 hours incubation and digested for another 2 hours. The digest reaction was then precipitated with Ethanol, centrifuged, the supernatant discarded, air dried and resuspended in 25 µl $dH_2O$ for electrophoresis.

Digested DNA samples were electrophoretically separated for approximately 4 hours at 45 volts on a 10×15 cm agarose gel using a 1× TAE running buffer. Following electrophoresis the gel was denatured (1.5M NaCl, 0.5M NaOH) then neutralised (1.5M NaCl, 0.5M Tris-base) before capillary transfer to positively charged nylon membrane (Hybond $N^+$) using the alkali method as described by the supplier (GE Healthcare, Buckinghamshire, England). The transferred DNA's were fixed to the membrane using Stratalinker (Stratagene, La Jolla, Calif., USA) following the manufacturer's recommendations. Membranes were stored at 4° C. between blotting paper in a plastic bag until required.

A DNA probe was synthesised using the PCR-based labelling reaction incorporating alkali-labile digoxigenin-11-dUTP (DIG, Roche Diagnostics, Basel, Switzerland). Template DNA was amplified from the hygromycin phosphotransferase gene in pCORF135 using primers rghlcpf (5'-3', AATACGAGGTCGCCAACATCT—SEQ ID NO: 30) and rghcpr (5'-3', AGGAACCCTAATTCCCTTATCTG—SEQ ID NO: 31) as described by Bajaj et al 2006 (Plant Cell Reports).

Nylon membranes were pre-hybridised using the DIG Easy Hyb Kit (Roche Diagnostics, Basel, Switzerland) for 1 hour at 42° C. The DIG-labelled probe was denatured (95° C., 5 minutes) and added to the pre-hybridisation solution and the membranes hybridised for approximately 12 hours at 42° C.

Following hybridisation membranes were subjected to two 5 minute washes in Low Stringency Wash Buffers (2×SSC, 0.1% SDS (w/v)) at room temperature with shaking, followed by two 15 minute washes in High Stringency Wash Buffer (0.1×SSC, 0.1% SDS (w/v)). Further washes were performed using the DIG and Wash and Block Buffer Set (Roche Diagnostics, Basel, Switzerland). Membranes were then incubated for 30 minutes at room temperature with Blocking Solution containing anti-DIG-AP antibody (Roche Diagnostics, Basel, Switzerland). Hybridised probes were then detected with the application of CDP-Star (Roche Diagnostics, Basel, Switzerland) chemiluminescent substrate for alkaline phosphatase. Membranes were heat-sealed in a plastic bag, exposed to X-ray film (Kodak BioMax MS, Rochester, N.Y.) ranging from 60 minutes to overnight and in a 100 Plus automatic developer.

Figure 12:
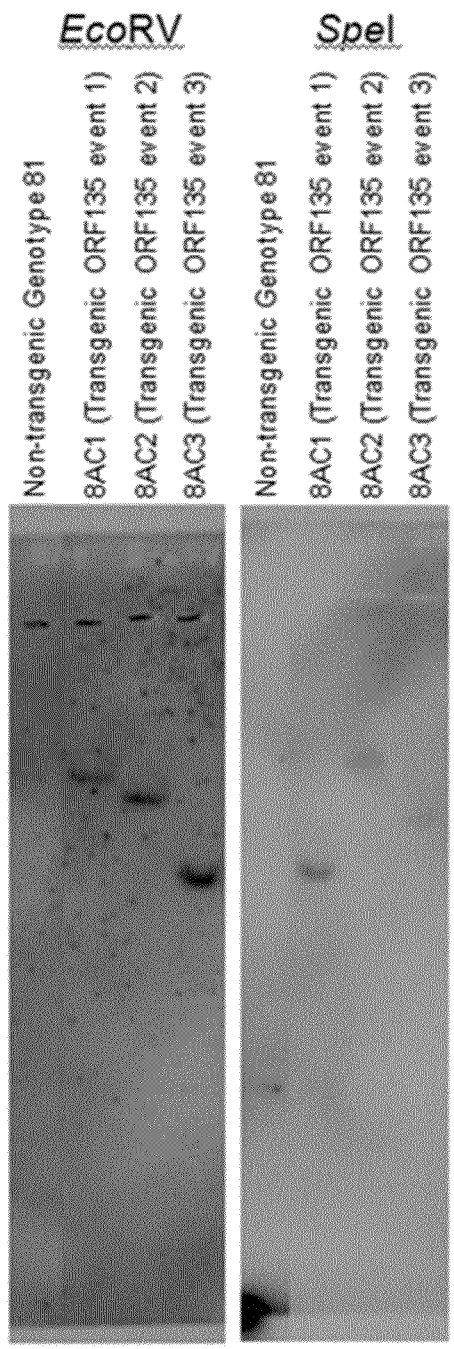
FIG. 12 shows southern-blot analysis for gene integration number determination.

The results in FIG. 12 show that each of the transgenic ORF135 events 1, 2 and 3 are transgenic for the pCORF135 T-DNA.

Example 4

Figure 6:
FIG. 6 shows the experimental set-up of plants prior to the application of drought-stress.
Figure 7:
FIG. 7 shows the condition of non-stressed plants (top left background) and stressed plants (foreground) after 10-days of drought-stress.
Figure 8:
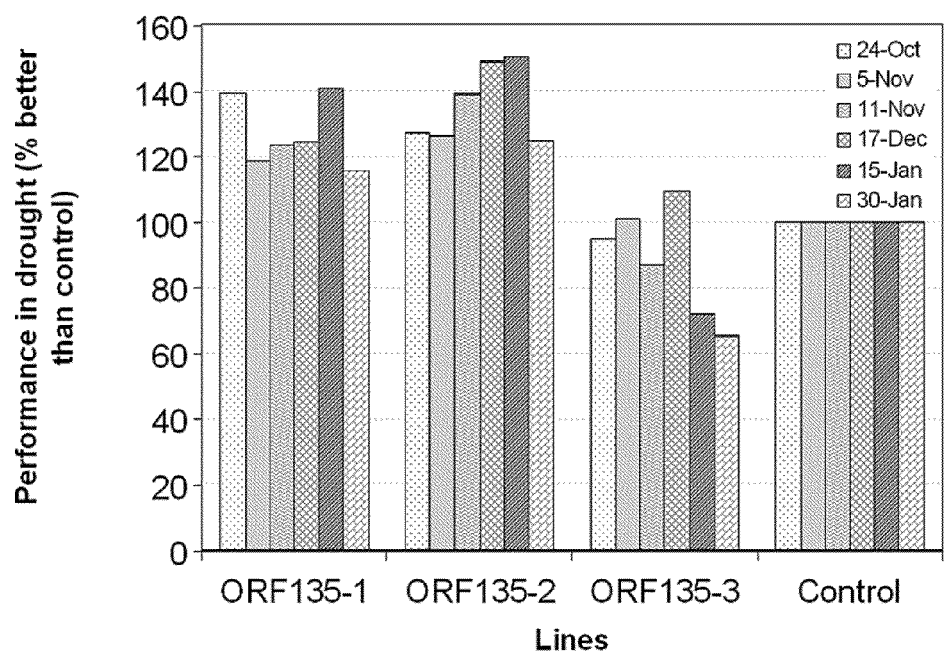
FIG. 8 shows the performance by different ryegrass lines (ORF135-1, ORF135-2, and ORF135-3) in drought as a percentage of the performance of the non-transgenic control ryegrass lines (control) in drought over a three month period.
Figure 9:
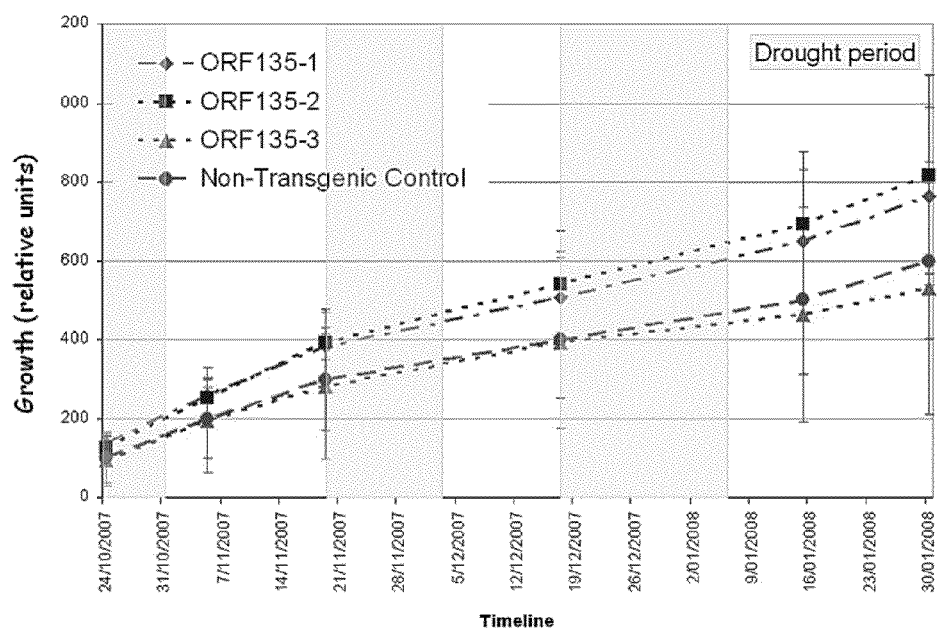
FIG. 9 shows the drought tolerance as determined by increase in relative dry weights in three $T_0$ (ORF135-1, ORF135-2, and ORF135-3) and one non-transgenic control line (control) during the 98 days of screening, which involved three progressively increasing drought periods (shaded portion of the timeline).

Alteration in Tolerance to Environmental Stress in Plants Transformed with Polynucleotides of the Invention Drought Screening in Growth Chamber The system was built of one meter long; 90 mm diameter plastic storm-water pipes. The pipes were placed on a mobile tray and supported at the sides by ropes and metal frame. The tubes were plugged at the bottom with rockwool and progressively filled with washed mortar sand using water to achieve uniform packing. At the center of the open end of each tube a clump of perennial ryegrass (25 tillers) was planted. There were three independent transgenic events (ORF135-1, ORF135-2 and ORF135-3) and each event was planted in six tubes. The plants were arranged at random, one in each of the six replicates, and grown at 70% relative humidity; 16/8 hours day/night cycle and under 650 $\mu mol.m^{-2}.s^{-1}$ light intensity. The plants were irrigated daily once in the morning with 50 mL Hoagland's solution (Hoagland and Arnon, 1938) and again in the afternoon with 50 mL plain water. The plants were acclimated initially for seven days and then the plants were trimmed back to 15 cm height. All plants were allowed to recover from trimming for the next seven days (FIG. 6). Drought-stress was imposed only on three of the six replicates after this recovery period by withholding the application of Hoagland's solution and water. During the drought screening, all plants were subjected to 50% relative humidity; 16/8 hours day/night cycle and 650 $\mu mol.m^{-2}.s^{--1}$ light intensity. The drought-stress was carried out for eight days when the volumetric water content in the sandy soil was less than 1% at 12 cm depth. The volumetric water content in the control, hydrated plants was greater than 10% at 12 cm depth. The drought-stress was stopped (FIG. 7) and irrigation resumed to the drought-stressed plants. All plants were also returned to 70% relative humidity; 16/8 hours day/night cycle and 650 $\mu mol.m^{-2}.s^{-1}$ light intensity. After four days, plant height was measured and then trimmed down to 15 cm height. The fresh-weight of the trimmed sample was measured and the samples were dried down for recording the dry weight. After 15 days, the plants were trimmed back to 15 cm height and once again the trimmed sample was measured for fresh and dry weight. A second drought regime lasting for 15 days was established immediately after trimming the plants. The humidity level, day-length, light intensity, etc were maintained at the same level as in the first drought period. The plants were then allowed to grow under irrigated conditions for 14 days. After this growth period, the plants were trimmed back to 15 cm height and the biomass used for recording fresh weight and dry weight. A third drought regime lasting for 21 days was initiated immediately and the humidity level, day-length, light intensity, etc were once again maintained at the same level as in the first drought period. Fresh weight and dry weight were recorded off the tissue obtained by trimming the plants back to 15 cm on the $10^{th}$ day after cessation of the third drought. The plants were continued to be grown under irrigated conditions for 15 more days and then data pertaining to fresh weight and dry weight were measured by trimming the plants back to 15 cm. Our analysis indicates that clones from two (ORF135-1 and ORF135-2) of the three regenerated plants were better at tolerating drought-stress than the clones from the non-transgenic control plant (FIGS. 8 and 9).

Soil Moisture Monitoring

The soil moisture (VWC, volumetric water content) was recorded with a Field Scout™ TDR 100 Soil Moisture Meter (Spectrum Technologies, Inc., IL, USA) as necessary. Measurements were taken in each tube at 12 cm depth and the average of three readings recorded. Following the establishment period subsurface irrigation was cut off. Soil moisture content declined and reached volumetric water content (VWC) below 1.0%. A period of no-irrigation was followed by a re-growth period.

Above-Ground Biomass

Leaf clipping dry weight was determined before (>10% VWC) and after drought stress (<1.0% VWC). All leaves were cut at 15 cm clipping height. The fresh weights (FW) of leaves were measured immediately, then leaves were dried at 80° C. for 48 h and the dry weight (DW) was measured. The ability to grow under drought-stress is calculated as percentage of inverse mass loss, which is calculated as the difference of dry weight in non-stressed and drought-stressed conditions over dry weight in non-stressed condition, i.e. (1-[{dry weight in non-stressed condition-dry weight in drought-stressed condition}/dry weight in non-stressed condition]) %.

Quantitative Real-Time PCR (qRT-PCR)

Leaf samples from the clones of the three $T_0$ regenerants and the non-transgenic control and also that which did not belong to the drought experiment was used for performing qRT-PCR. Plant leaves were frozen in liquid nitrogen and then ground to a fine powder using a mortar and pestle and liquid nitrogen. Total RNA was extracted from the ground leaves using Qiagen Plant RNeasy kit and RNAseI-free DNAse I (Qiagen). First strand cDNA was synthesised from 5 µg total RNA using Superscript™ III reverse transcriptase (Invitrogen) using manufacturer's protocol. A 15-µL aliquot of the first-strand cDNA was diluted with 35 µL sterile water and then used in the carrying out the quantitative real-time polymerise chain (qRT-PCR) analysis. Concentration of each transcript was measured in ABI Prism 7700 (Applied BioSystems) using the Sybr Green technology in 25 µL PCR-mix using 5 µL of the diluted first-strand cDNA. Transcript levels for chlorophyll AB binding protein (CAB—reference gene), hptII and cloned sORF were monitored. The sequence of the primers used were as follows:

```
CAB forward primer
                                     (SEQ ID NO: 24)
5'GTCTCGACTACCTCGGCAAC3';

CAB reverse primer
                                     (SEQ ID NO: 25)
5'ACCGAACATGGAGAACATGG3';

hptII forward primer
                                     (SEQ ID NO: 26)
5'AATACGAGGTCGCCAACATCT3' hptII reverse primer
                                     (SEQ ID NO: 27)
5'AGGAACCCTAATTCCCTTATCTG3';

cloned sORF forward primer
                                     (SEQ ID NO: 28)
5'GAAGAGCTAGGGTTTGGTCGAGAGGA3';
and cloned sORF reverse primer
                                     (SEQ ID NO: 29)
5'AGGAACCCTAATTCCCTTATCTG3'.
```

Figure 10:
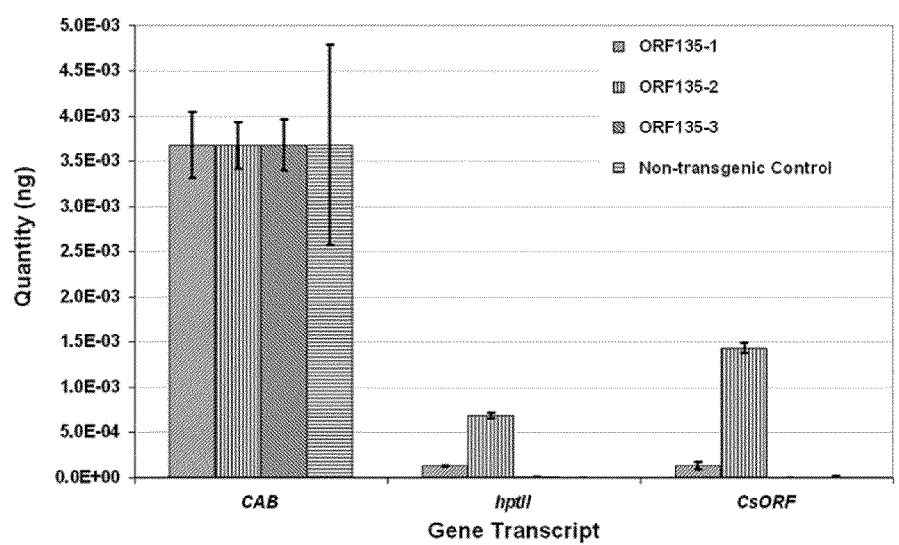
FIG. 10 shows qRT-PCR analysis of transcripts in one non-transgenic control (control) and three independent $T_0$ lines (ORF135-1, ORF135-2, and ORF135-3).

The thermal cycling conditions were as follows: stage 1: 94° C. for 10 minutes, 1 cycle; stage 2: 94° C. for 15 seconds, 55° C. for 15 seconds, 72° C. for 1 minute, 40 cycles; dissociation protocol set to 60° C. Known quantities of five serial dilutions of CAB standards were used for quantifying amplicons. The amplicon quantities were compared against the level of normalized chlorophyll AB binding protein gene transcript in the same sample to calculate the relative gene expression levels (see FIG. 10). From this analysis, we have reason to believe that one (ORF135-3) of the three regenerated $T_0$ plant is an escape or one where the transgenes have been silenced probably by methylation. The lack of the transgene expression in this $T_0$ plant could explain the poor performance by the clones of these (ORF135-3) plants (relative to ORF135-1 and ORF135-2) when challenged with drought.

The above examples illustrate practice of the invention. It will be appreciated by those skilled in the art that numerous variations and modifications may be made without departing from the spirit and scope of the invention.

Summary of Sequences:

| SEQ ID NO: | Sequence type | Information | Species |
|---|---|---|---|
| 1 | polynucleotide | ORF135 cDNA | *Lolium perenne* |
| 2 | polynucleotide | gb|EF143989/ABO42268.1 | *Hordeum vulgare* |
| 3 | polynucleotide | gb|EF576051/ABR25639.1 | *Oryza saliva indica* |
| 4 | polynucleotide | gb|NM_001054024/NP_001047489.1 | *Oryza saliva japonica* |
| 5 | polynucleotide | gb|NM_123595/NP_199045.1 | *Arabidopsis thaliana* |
| 6 | polynucleotide | gb|EF146221/ABK94311.1 | *Populus trichocarpa* |
| 7 | polynucleotide | gb|EF083088/ABK22439.1 | *Picea sitchensis* |
| 8 | polynucleotide | gb|XM_001783715/XP_001783767.1 | *Physcomitrella patens* |
| 9 | polynucleotide | gb|XM_001420059/XP_001420096.1 | *Ostreococcus lucimarinus* |
| 10 | polypeptide | ORF135 cDNA | *Lolium perenne* |
| 11 | polypeptide | gb|AB042268.1 | *Hordeum vulgare* |
| 12 | polypeptide | gb|ABR25639.1 | *Oryza saliva indica* |
| 13 | polypeptide | gb|NP_001047489.1 | *Oryza saliva japonica* |
| 14 | polypeptide | gb|NP_199045.1 | *Arabidopsis thaliana* |
| 15 | polypeptide | gb|ABK94311.1 | *Populus trichocarpa* |
| 16 | polypeptide | gb|ABK22439.1 | *Picea sitchensis* |
| 17 | polypeptide | gb|XP_001783767.1 | *Physcomitrella patens* |
| 18 | polypeptide | gb|XP_001420096.1 | *Ostreococcus lucimarinus* |
| 19 | polypeptide | Viridiplantae consensus | artificial |
| 20 | polypeptide | Magnoliophyta [flowering plant] consensus | artificial |
| 21 | polypeptide | monocotyledonous consensus | artificial |
| 22 | polypeptide | dicotyledonous consensus | artificial |
| 23 | polynucleotide | vector, ORF135 | artificial |
| 24 | polynucleotide | CAB forward primer | artificial |
| 25 | polynucleotide | CAB reverse primer | artificial |
| 26 | polynucleotide | hptII forward primer | artificial |
| 27 | polynucleotide | hptII reverse primer | artificial |
| 28 | polynucleotide | cloned sORF forward primer | artificial |
| 29 | polynucleotide | cloned sORF reverse primer | artificial |
| 30 | polynucleotide | rghlcpf primer | artificial |
| 31 | polynucleotide | rghcpr primer | artificial |

The invention claimed is:

1. A method of producing a plant with altered tolerance to drought, the method comprising:
   (i) transforming a plant cell with:
      a) a polynucleotide comprising the sequence of SEQ ID NO: 1;
      b) a polynucleotide comprising the coding sequence set forth in SEQ ID NO: 1;
      c) a polynucleotide encoding a polypeptide comprising the sequence of SEQ ID NO: 10; or d) a polynucleotide comprising the complement of the polynucleotide of any one of a) to c), and
   (ii) regenerating a transgenic plant from said plant cell,
   (iii) applying drought conditions to said regenerated plant,
   (iv) selecting a plant for altered drought tolerance in comparison to a plant not transformed with said polynucleotide, and
   (v) obtaining the selected plant.

2. The method of claim 1 in which the altered tolerance is increased tolerance.

3. The method of claim 1 in which the plant cell is transformed with a genetic construct, expression construct, or vector comprising the polynucleotide.

4. The method of claim 1 further comprising collecting seeds from the obtained plant, wherein said seeds comprise the polynucleotide.

5. The method of claim 1, wherein the plant cell is transformed with a polynucleotide comprising the sequence of SEQ ID NO: 1.

6. The method of claim 1, wherein the plant cell is transformed with a polynucleotide comprising the coding sequence set forth in SEQ ID NO: 1.

7. The method of claim 1, wherein the plant cell is transformed with a polynucleotide encoding a polypeptide with the amino acid sequence of SEQ ID NO: 10.

* * * * *